(12) United States Patent
Chiu et al.

(10) Patent No.: US 10,357,579 B2
(45) Date of Patent: Jul. 23, 2019

(54) DEVICE PORT CLEANER

(71) Applicant: Texas Medical Group SOPARFI S.a.r.l., Luxembourgh (LU)

(72) Inventors: Aaron Chiu, El Paso, TX (US); Enrique Delgado Macias, Chihuaha (MX); Cesar Aguilera, Chihuahua (MX)

(73) Assignee: Texas Medical Group Soparfi S.A.R.L., Luxembourg (LU)

( * ) Notice: Subject to any disclaimer, the term of this patent is extended or adjusted under 35 U.S.C. 154(b) by 0 days.

(21) Appl. No.: 15/062,968

(22) Filed: Mar. 7, 2016

(65) Prior Publication Data

US 2017/0232121 A1    Aug. 17, 2017

Related U.S. Application Data

(60) Provisional application No. 62/237,234, filed on Oct. 5, 2015.

(51) Int. Cl.
| | | |
|---|---|---|
| A61L 2/00 | (2006.01) | |
| A61B 1/00 | (2006.01) | |
| A61M 37/00 | (2006.01) | |
| G07F 11/72 | (2006.01) | |
| B08B 3/00 | (2006.01) | |
| A61B 90/70 | (2016.01) | |
| A61L 2/18 | (2006.01) | |
| B08B 3/06 | (2006.01) | |
| B08B 7/04 | (2006.01) | |
| A61M 5/00 | (2006.01) | |
| A61M 39/16 | (2006.01) | |
| B08B 3/04 | (2006.01) | |
| B08B 3/10 | (2006.01) | |
| B08B 9/00 | (2006.01) | |
| A61M 5/31 | (2006.01) | |

(52) U.S. Cl.
CPC ............... *A61L 2/00* (2013.01); *A61B 90/70* (2016.02); *A61L 2/18* (2013.01); *A61M 5/001* (2013.01); *A61M 39/16* (2013.01); *B08B 3/00* (2013.01); *B08B 3/04* (2013.01); *B08B 3/044* (2013.01); *B08B 3/06* (2013.01); *B08B 3/10* (2013.01); *B08B 7/04* (2013.01); *B08B 9/00* (2013.01); *A61M 2005/3104* (2013.01)

(58) Field of Classification Search
CPC .... B08B 3/00; B08B 7/04; B08B 3/06; B08B 1/003; A61M 39/162
USPC ................ 422/292; 134/93, 166 R; 600/133; 604/84; 221/30, 92, 302
See application file for complete search history.

(56) References Cited

U.S. PATENT DOCUMENTS

| | | | |
|---|---|---|---|
| 5,554,135 A * | 9/1996 | Menyhay | ............ A61M 39/162 138/89 |
| 6,419,825 B1 * | 7/2002 | Hahmann | ............ A61M 1/169 210/232 |
| 7,780,794 B2 | 8/2010 | Rogers et al. | |
| 7,985,302 B2 | 7/2011 | Rogers et al. | |

(Continued)

FOREIGN PATENT DOCUMENTS

CN           103285413 A       9/2013

*Primary Examiner* — Monzer R Chorbaji
(74) *Attorney, Agent, or Firm* — Carr Law Firm PLLC

(57) ABSTRACT

The present invention includes a device cleaner, and method of use, for cleaning a device port, particularly a medical device port, that may be inserted into the device port cleaner for cleaning and/or disinfecting.

45 Claims, 21 Drawing Sheets

(56) References Cited

U.S. PATENT DOCUMENTS

| | | | |
|---|---|---|---|
| 8,065,773 | B2 | 11/2011 | Vaillancourt et al. |
| 8,172,825 | B2 | 5/2012 | Solomon et al. |
| 8,206,514 | B2 | 6/2012 | Rogers et al. |
| 8,252,247 | B2 * | 8/2012 | Ferlic .................. A61L 2/235 422/309 |
| 8,336,152 | B2 | 12/2012 | Vaillancourt et al. |
| 8,388,894 | B2 | 3/2013 | Colantonio et al. |
| 9,192,443 | B2 | 11/2015 | Tennican |
| 9,750,929 | B2 | 9/2017 | Ma et al. |
| 2006/0030827 | A1 | 2/2006 | Raulerson et al. |
| 2010/0050351 | A1 | 3/2010 | Colantonio et al. |
| 2011/0030726 | A1 | 2/2011 | Vaillancourt et al. |
| 2011/0314619 | A1 | 12/2011 | Schweikert |
| 2012/0111368 | A1 | 5/2012 | Rahimy et al. |
| 2013/0323117 | A1 * | 12/2013 | Ma ..................... A61M 39/16 422/1 |
| 2015/0273199 | A1 * | 10/2015 | Adams ................ A61M 39/16 604/256 |

\* cited by examiner

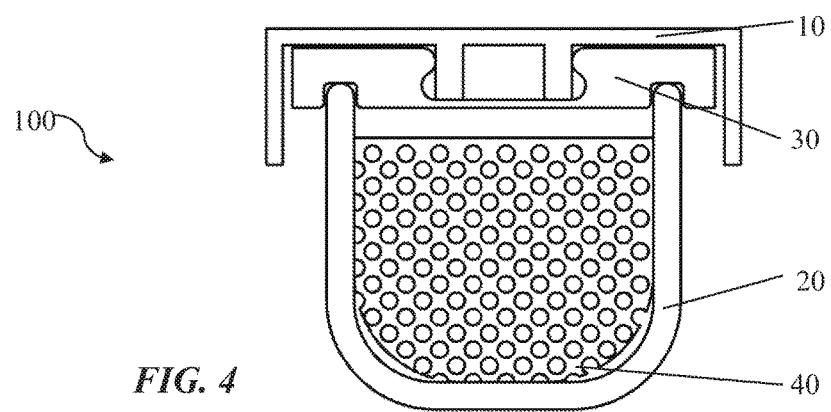
FIG. 4
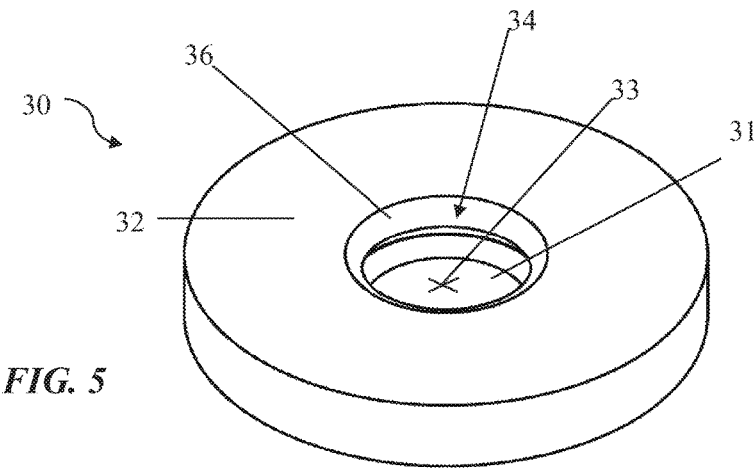
FIG. 5
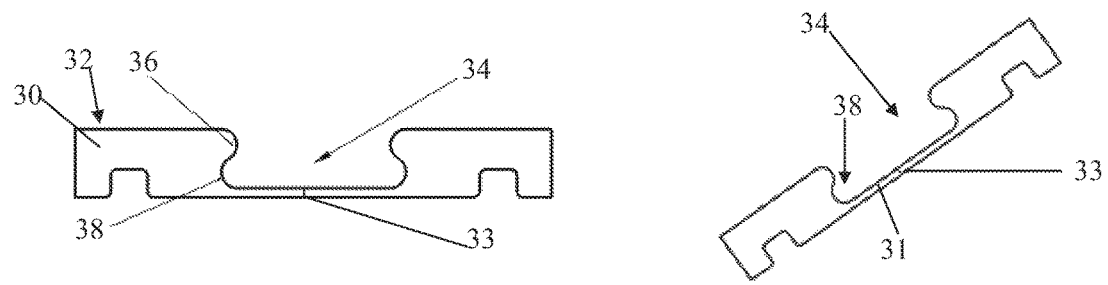
FIG. 6A
FIG. 6B

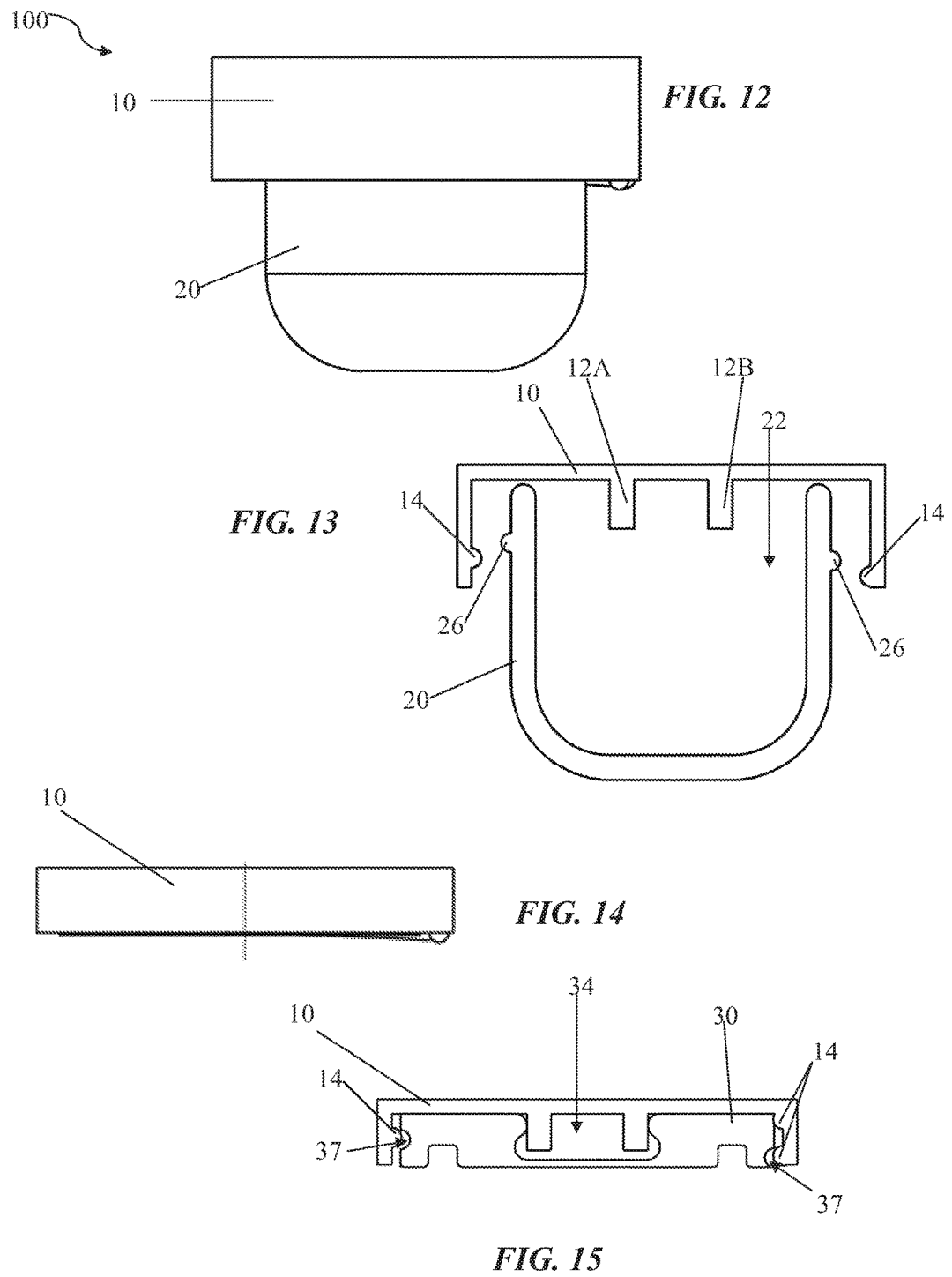

US 10,357,579 B2

DEVICE PORT CLEANER

CROSS-REFERENCE TO RELATED APPLICATIONS

The application relates to, and claims the benefit of the filing date of, U.S. provisional patent application Ser. No. 62/237,234 entitled "DEVICE PORT CLEANER," filed Oct. 5, 2015, the entire contents of which are incorporated herein by reference for all purposes.

BACKGROUND OF THE INVENTION

Field of the Invention

The present invention relates to device ports, and more particularly to an apparatus and a method for cleaning and/or decontaminating device ports, including medical device ports.

Description of the Related Art

When treating patients in the medical field, there is a need to prevent the transmission. of pathogens into or onto a patient from a potentially contaminated surface of a medical implement, or "site" when infusing fluids or aspiration of fluids to or from a patient. Such pathogens include microorganisms such as bacteria and viruses. The transmission of pathogens into a patient may result in an infection that could be life threatening. Traditionally, cleaning a potentially contaminated surface includes a protocol of alcohol swabbing prior to making the necessary connections to the site. However, a poorly swabbed site can carry microorganisms that, if allowed to enter a patient's body, can cause serious harm. Sometimes, much of medical implements used may be so small that it may be difficult to properly cleanse all portions of the implement, particularly the connecting portions of medical device ports. Even more difficult is the ability to clean the interior surface of device ports that are difficult to access. Therefore, it is desired to provide a cleaning device that is simple, economical to manufacture, and effective in cleaning the interior and exterior surface of device ports, particularly medical device ports.

SUMMARY

Provided is a device port cleaner, and method of use, for cleaning a device port that may be inserted into the device port cleaner.

BRIEF DESCRIPTION OF THE DRAWINGS

For a more complete understanding of the features and advantages thereof, reference is now made to the following Detailed Description taken in conjunction with the accompanying drawings, in which:

FIG. 4 illustrates a cross-sectional view of the device port cleaner;

FIG. 5 illustrates a perspective view of an embodiment of the membrane;

FIGS. 6A and 6B illustrate a cross-sectional view of the membrane;

FIGS. 12 and 13 illustrate the lid being secured directly over an opening in a reservoir of the device port cleaner;

FIGS. 14 and 15 illustrate the lid being secured directly to the membrane of the device port cleaner;

DETAILED DESCRIPTION OF THE INVENTION

In the following discussion, numerous specific details are set forth to provide a thorough understanding of the present invention. However, those skilled in the art will appreciate that the present invention may be practiced without such specific details. In other instances, certain specific details, and the like have been omitted inasmuch as such details are not considered necessary to obtain a complete understanding of the present invention, and are considered to be within the understanding of persons of ordinary skill in the relevant art.

In FIGS. 1-15, a device port cleaner 100 is shown. In an embodiment, the device port cleaner 100 may be used to clean and sterilize a device port. The device port cleaner 100 may clean the device port by inserting at least a portion of the device port into the device port cleaner 100. According to such an embodiment, the device port cleaner 100 may clean various device ports such as medical device ports, needle ports, needleless ports, leer locks, catheter hubs, and the like. The device port cleaner 100 may also be used with threaded male and female connectors used with infusion therapies such as but not limited to intravenous lines, pharmaceuticals, chemotherapeutic drugs, supplements, intrathecal, and the like.

Figure 1:
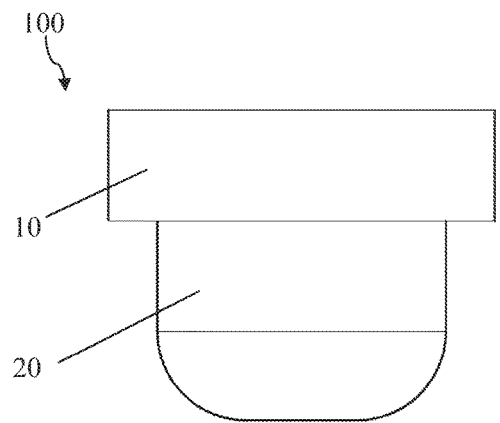
FIGS. 1 and 2 illustrate an embodiment of a device port cleaner.
Figure 2:
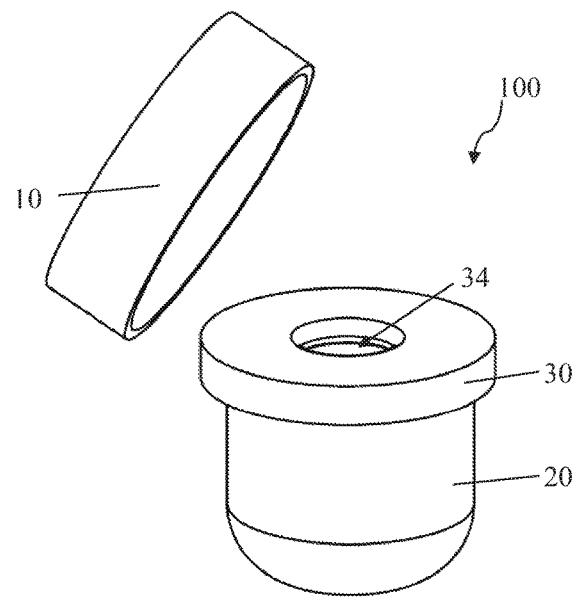
Figure 3:
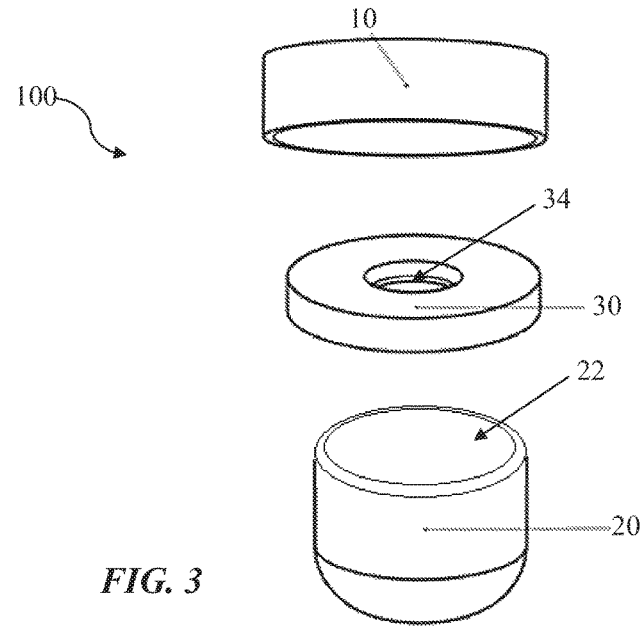
FIG. 3 illustrates an exploded view of the device port cleaner.

Turning to FIGS. 1-3, an embodiment of the device port cleaner 100 is shown. The device port cleaner 100 may comprise a reservoir 20, a membrane 30 and a lid 10. The reservoir 20 may comprise an opening 22 that the device port may be inserted into. The membrane 30 may be secured over the opening 22 to create a seal within the reservoir 20. The lid 10 may be positioned over the membrane 30 and the opening 22 to protect the membrane 30 secured over the opening 22. When lid 10 is secured on the device port cleaner 100, the membrane 30 may be positioned between the lid 10 and the reservoir 20. The membrane 30 may seal over the opening 22 of the reservoir 20 to protect the interior of the reservoir 20 from the external environment or contaminants before being used. The lid 10 may be positioned over both the reservoir 20 and the membrane 30 to protect the membrane 30 from being inadvertently damaged or punctured prior to use.

The reservoir 20 may be substantially a container capable of holding a disinfecting agent 40 and receiving a device port through the opening 22. In the embodiment shown in FIG. 3, the reservoir 20 may be formed like a round cup. The reservoir 20 may comprise an opening 22 that a port device may be inserted into. However, various shaped containers known to one of ordinary skill in the arts may be used when forming the reservoir 20. For an example, the reservoir 20 may be formed using various hollowed out structures such as a cube, prism, cylinder, cone, and the like. The reservoir 20 may be made of various semi-rigid to rigid materials, including plastic, aluminum, polymer, stainless steel, silicone based material, synthetic isoprene, isoprene, thermoplastics, and the like. It should be appreciated by one skilled in the art that a wide range of materials or mixtures of materials, with properties similar to the above-listed materials may be used to construct the reservoir 20 of the device port cleaner 100. The cutout forming the opening 22 in the reservoir 20 may also be of various shapes. The shape of opening 22 may depend on the shape of the device port intended to be inserted into the device port cleaner 100 for cleaning. The opening 22 may be formed to be similar to the overall shape of the reservoir 20. For example, the opening 22 may be shaped to be a square cutout, a rectangular cutout, a conical cutout, and the like.

In FIG. 4, the reservoir 20 of the device port cleaner 100 may contain a disinfecting agent 40 for cleaning device ports inserted into the device port cleaner 100. The disinfecting agent 40 may be any antimicrobial or antiseptic agent including ethyl alcohol, medical grade alcohol, isopropyl alcohol, povidone iodine, and the like. The disinfecting agent 40 may also be in a liquid, gel, or hydrogel form with various viscosities. The disinfecting agent 40 may be initially sealed within the reservoir 20 by the membrane 30 of the device port cleaner 100 until exposed to a device port inserted into the device port cleaner 100. The reservoir 20 containing the disinfecting agent 40 may be sealed by the membrane 30 to prevent the disinfecting agent 40 from leaking out of the device port cleaner 100 prior to use. The membrane 30 may also separate and protect the interior of reservoir 20 and the disinfecting agent 40 from the external environment or contaminants.

Turning to FIGS. 5, 6A, and 6B, the membrane 30 may comprise a bulb cavity 34 positioned near the center of the membrane 30. The bulb cavity 34 may further comprise an upper lip ring 36 and a widened contour groove 38. The upper lip ring 36 may be positioned along the circumference of the opening of the cavity 34 adjacent to the outer surface 32 of the membrane 30. The upper lip ring 36 may extend from the outer surface 32 of the membrane 30 towards the interior opening of the cavity 34. The extension of the upper lip ring 36 may be formed by the widened contour groove 38 cutout adjacent and below the upper lip ring 36. The widened contour groove 38 may be formed by a circumferential rounded cutout along the interior surface of bulb cavity 34 while leaving a portion of the membrane 30 and the top surface 32 intact. The widened contour groove 38 cutting into the interior portion of the membrane 30 may form the upper lip ring 36 extending along the outer surface 32. The upper lip ring 36 may extend over the widened contour groove 38 towards the interior of the bulb cavity 34.

The widened contour groove 38 may outline a base 31 of the cavity 34. The base 31 may further comprise a slit 33 that allows for the insertion of a device port. The base 31 may be opposite of the upper lip ring 36 and the opening of the cavity 34. The membrane 30 may be made of a material capable of creating a tight seal that may isolate the disinfecting agent 40 from the outside environment and containments. Furthermore, the membrane 30 may comprise an elastic material to enable the membrane to adapt to the specific shapes of different inserted device ports. In an embodiment, the membrane 30 may be made of various materials including silicone, polymer, synthetic isoprene, isoprene, polymer, thermoplastics, thermoplastic polymers, thermoplastic elastomers, and the like.

Figures 7, 8:
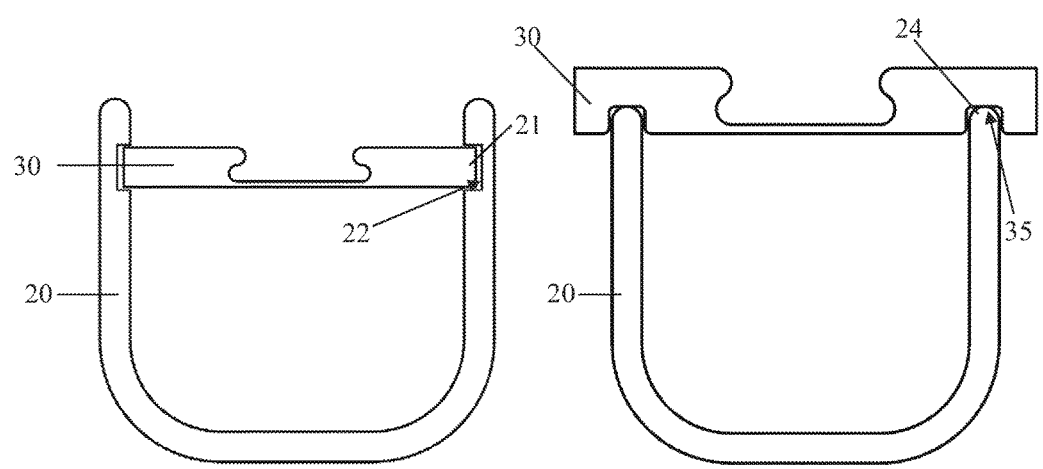
FIGS. 7 and 8 illustrate additional embodiments of the device port cleaner with the membrane being attached along the interior and the exterior of the cleaner, respectively.

In the embodiment shown in FIGS. 7 and 8, the membrane 30 may be secured over the opening 22 to seal the interior of the reservoir 20. The membrane 30 may seal off the opening 22 by being secured along the interior surfaces of the reservoir 20, or exteriorly around the outer circumference of the opening 22. As shown in FIG. 7, the membrane 30 may be attached interiorly by positioning the outer edge 21 of the membrane 30 within an indentation 22 along the inner walls of the reservoir 20. The membrane 30 may also be attached by other mechanical means or fasteners including an adhesive, a snap fit fastener, a loop retaining ring, and the like. In FIG. 8, the membrane 30 may be attached exteriorly by securing the membrane over the top edge 24 of the reservoir 20. The membrane 30 may be secured exteriorly to the reservoir 20 mechanically by affixing the top edge 24 of the reservoir 20 into a circular indention 35 along the bottom surface of the membrane 30. The size and shape of the indention 35 in the membrane 30 may substantially match the size and shape of the top edge 24 of the reservoir 20. The membrane 30 may also be affixed over the opening 22 of the reservoir 20 with an adhesive, or retained by mechanical fasteners such as clips, bolts, rivets, clamps, and the like. The membrane 30 may also be bonded or affixed to the inner walls of the reservoir 20 without the indentions 22.

Figure 9A:
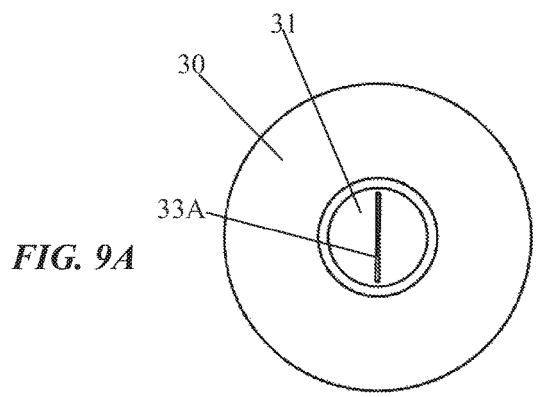
FIGS. 9A-9D illustrate a top view of additional embodiments of membrane with different slit configurations in the membrane, respectively.
Figure 9B:
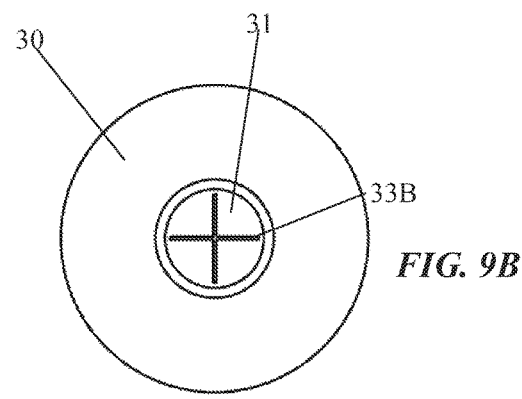
Figure 9C:
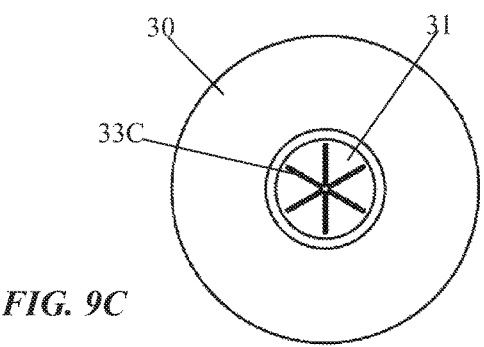
Figure 9D:
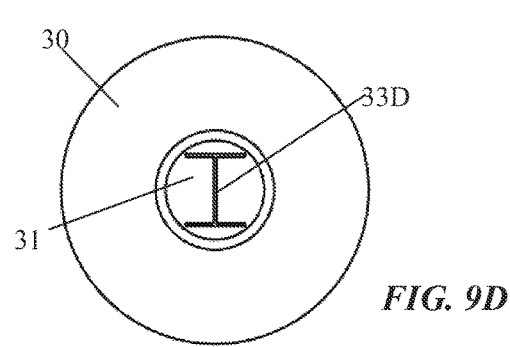

Turning to FIGS. 9A-9D, the slit 33 in the membrane 30 of the device port cleaner 100 may comprise various configurations to aid in maintaining a seal when the device port is inserted and penetrates the membrane 30. The slit 33 may allow the device port to access the interior of the reservoir 20 by functioning as a valve across the membrane 30. The slit 33 in the membrane 30 may allow for smooth passage of the device port through the membrane 30 to immerse the device port in the disinfecting agent 40. The slit 33 may function as a valve capable of maintaining the seal within reservoir 20 after being penetrated by the device port. FIGS. 9A-9D show a plurality of configurations for slit 33 that may be made in the membrane 30 to allow penetration of the device port through the membrane 30. In FIG. 9A, the membrane 30 may comprise a slit 33A formed by one concentric slit as shown. In FIG. 9B, the membrane 30 may comprise a slit 33B formed by two concentric slits substantially perpendicularly crossed. In FIG. 9C, the membrane 30 may comprise a slit 33C formed by four linear slits each crossed at the center of each of the other slits. In FIG. 9D the membrane 30 may comprise a slit 33D formed by three linear slits positioned in the shape of the letter "I."

The membrane 30 with slits 33A-33D may operate as a dynamic seal during the insertion or removal of the device port through the membrane 30. The membrane 30 with slits 33 may also operate as a static seal when the device port is inserted or removed. Following the removal of the device port inserted into the device port cleaner 100 for cleaning, the membrane 30, and the slits 33 may recover to their original positions re-sealing the reservoir 20. The slit 33 configurations may not be limited to only the examples shown, but may be expanded to include any other configuration known to one of ordinary skill that may enable an elastic membrane to maintain a seal around an area when pierced by an object. Alternatively, the location, quantity, shape, and size of the slit 33 may vary in accordance with the size of the reservoir 20, the dimensions, or specifications of the membrane 30, or the size of the device port the device port cleaner 100 may be intended to be used with. The slit 33 configurations shown in FIGS. 9A-9D may be made in the membrane 30 affixed over the top edge 24 of the reservoir 20 as well as in the membrane 30 affixed within the interior walls of reservoir 20. Alternatively, the membrane 30 may not comprise any slits 33 at all.

When the device port penetrates the membrane 30 to access the disinfecting agent 40 within the reservoir 20, the membrane 30 may continue to create a seal within the reservoir 20 while the device port is partially immersed within the disinfecting agent 40. The slit 33 in the membrane 30 may allow the device port to pierce the membrane 30 just enough for the device port to access the disinfecting agent 40 without exposing the sealed interior portion of the reservoir 20 to the external environment. The membrane 30 may still seal the disinfecting agent 40 within the reservoir 20 to disinfect the inserted device port while preventing leakage when the device port is partially inserted.

Figure 10:
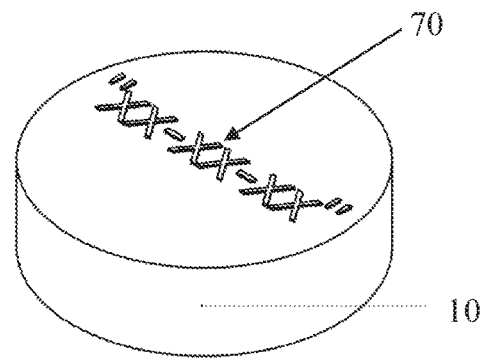
FIG. 10 illustrates an embodiment of the lid with identification data printed on the lid.

Turning to FIG. 10, in an embodiment, the lid 10 may be used to print various labels 70 and identification data relating to the device port cleaner 100 or the device port the cleaner 100 is intended to be used with. Other examples of labels that may be printed on the lid 10 may include but is not limited to the brand name, the manufacturing date, the contents within the reservoir 20, and the like.

Figure 11A:
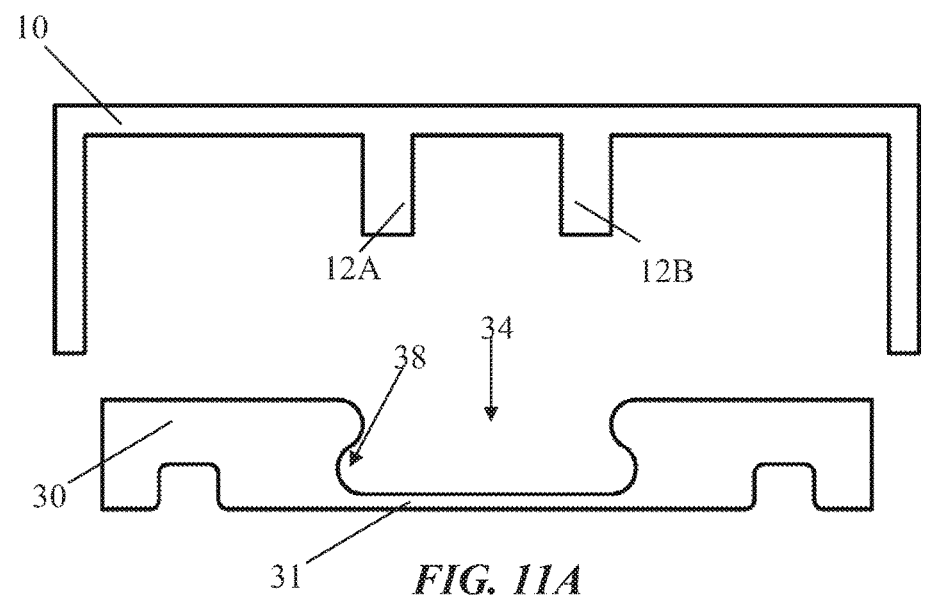
FIGS. 11A and 11B illustrate a cross-sectional view of a lid being pressed into a membrane of the device port cleaner.
Figure 11B:
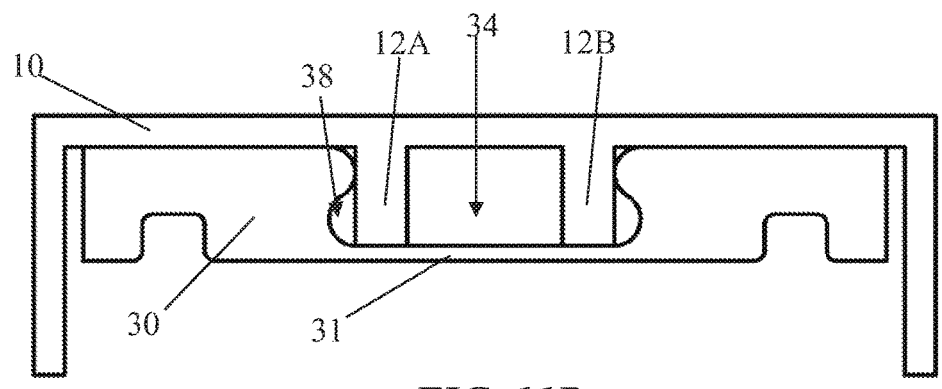

FIGS. 11A and 11B show an alternative embodiment of the lid 10 to further secure the lid 10 over the membrane 30 and the reservoir 20. In an embodiment as shown in FIG. 11A, the lid 10 may further comprise a pair of extrusions 12A, 12B that may be fitted into the bulb cavity 34 in membrane 30 to further support the coupling of the membrane 30 to the lid 10. The extrusions 12A, 12B in lid 10 may contact the lip ring 36 and base 31 of the cavity 34 when the lid 10 is fitted over the membrane 30 on to the reservoir 20. The extrusions 12A, 12B may also contact a portion of the widened contour groove 38. As shown in FIG. 12B, in an embodiment, the extrusions 12A, 12B fitted inside the cavity 34 when the lid 10 is secured may further support and maintain the formation of the cavity 34 during storage of the cleaner 100.

Referring to FIGS. 12-15, the lid 10 may be positioned over the membrane 30 and the opening 22 of the reservoir 20 to protect the membrane 30 prior to the device port being inserted into the device port cleaner 100. The outer diameter of the outer surface of the reservoir 20 may be sized to be slightly smaller than the interior diameter of the lid 10 such that the lid 10 may be fitted over the reservoir 20. The lid 10 may cover the membrane 30 and the opening 22 by being affixed to any one of the reservoir 20, the membrane 30, or both. FIGS. 12-13 show a lid 10 being affixed to the reservoir 20 directly. In FIG. 13, the lid 10 and the outer surface of the reservoir 20 may both further comprise threading that may be used to secure and thread the lid 10 over the reservoir 10 and the membrane 30. The lid 10 may further comprise a series of inner threading 14 extending along the interior circumference of the lid 10. The reservoir 20 may further comprise a series of outer threading 26 extending around the exterior surface and circumference of the reservoir 20. Lid 10 may be screwed onto the reservoir 20 by mating the inner threading 14 of the lid 10 with the outer threading 26 of the reservoir 20.

Turning to FIGS. 14 and 15, in another embodiment, the lid 10 may be directly affixed to the membrane 30 as shown. In FIG. 15, the lid 10 and the membrane 30 may be secured together by threading the lid 10 onto the membrane 30. The lid 10 may comprise an inner threading 14 along the interior surface of the lid 10. The membrane 30 may comprise a series of threaded cuts 37 around the exterior circumference of the membrane 30 that may couple with the inner threading 14 of lid 10. The threaded cuts 37 may be sized to fit the inner threading 14 formed along the interior surface of lid 10. The lid 10 may be screwed over the membrane 30 by mating the inner threading 14 of the lid 10 with the threaded cuts 37 in the membrane 30. Alternatively, the lid 10 may be a thin foil bonded over at least one of the opening 22 and the membrane 30. The lid 10 may then be peeled off prior to use. Alternatively, the lid 10 may be made of other materials including aluminum paper, aluminum polymer, polymer, nylon, and the like.

Figure 16:
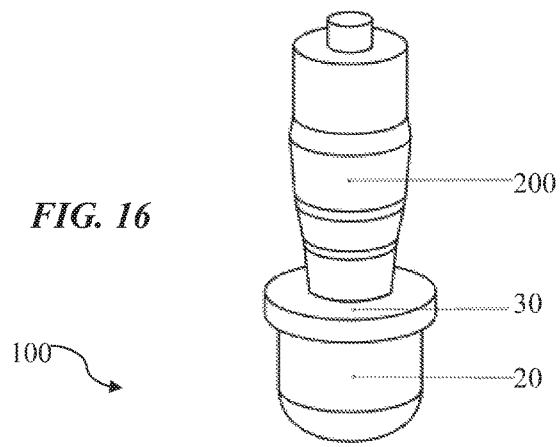
FIG. 16 illustrates the device port cleaner with a device port inserted through the membrane.

As shown in FIG. 16, a device port 200 may be inserted into the device port cleaner 100 to sterilize or disinfect a portion of the port 200. To use the device port cleaner 100, the lid 10 may first be removed from the cleaner 100 to expose the membrane 30. After removal of the lid 10, the device port 200 may be inserted into the device port cleaner 100 by penetrating the membrane 30 with the port 200 to access the reservoir 20.

Figures 17, 18:
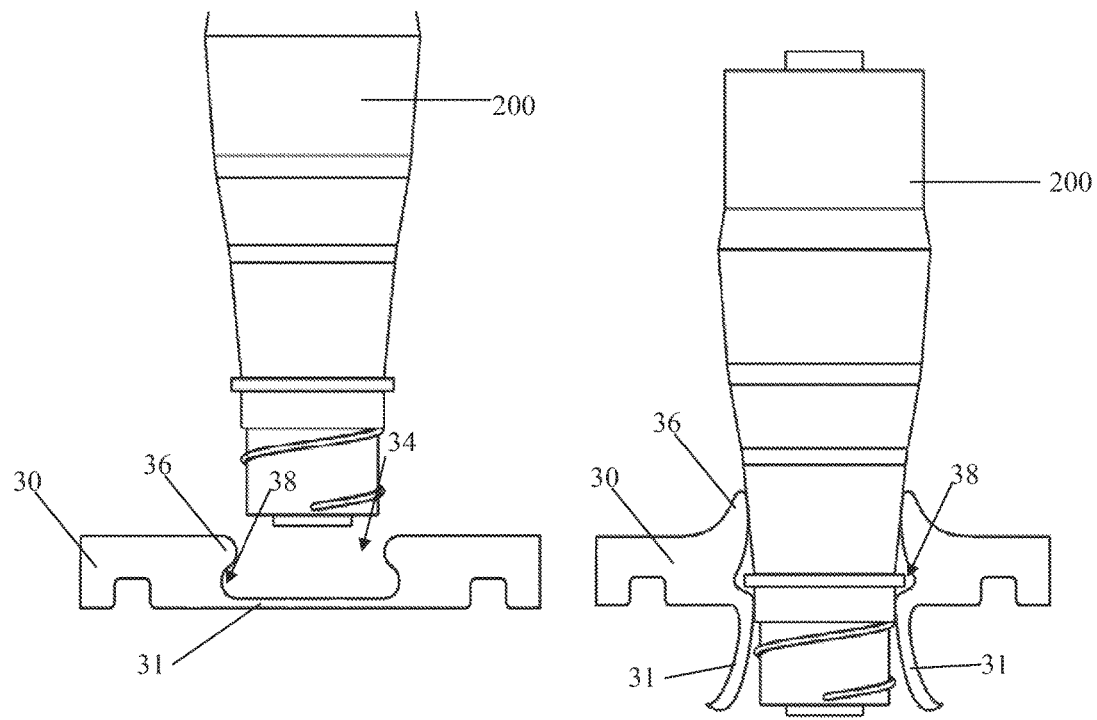
FIGS. 17 and 18 illustrate a cross-sectional view of a device port being inserted into embodiment of the membrane of the device port cleaner.

Turning to FIGS. 17 and 18, the device port 200 may access the reservoir 20 by penetrating the membrane 30. The device port 200 may be inserted into the reservoir 20 through the base 31 of the bulb cavity 34. The device port 200 may penetrate the slit 33 in base 31. The upper lip ring 36 of the bulb cavity 34 may be formed from an elastic material such that the ring 36 may accommodate for the geometry of the device port 200. As the device port 200 is inserted into the bulb cavity 34, the upper lip ring 36 expands to contact the outer circumference of the device port 200. In FIG. 18, as the device port 200 penetrates the base 31 of the membrane 30, the upper lip ring 36 may contact the device port 200 and form a seal. After the membrane 30 is initially penetrated by the port 200, a portion of the penetrated base 31 formed from the slits 33 may remain in contact with the device port 200 such that a second contact point and seal may be formed between the base 31 and the device port 200. When the membrane 30 is penetrated by the port device 200 to access the reservoir 20, the lip seals formed by the upper lip ring 36 and the base 31, with the device port 200, may allow the membrane 30 to maintain the seal within the reservoir 20 while the device port 200 is being inserted. The lip seals may also operate to prevent leakage of the disinfecting agent 40 when the device port 200 is inserted into the reservoir 20. The lip seal and the membrane 30 may also physically support the insertion and position of the device port 200 when the device port 200 is inserted into the device port cleaner 100.

Figures 21, 22:
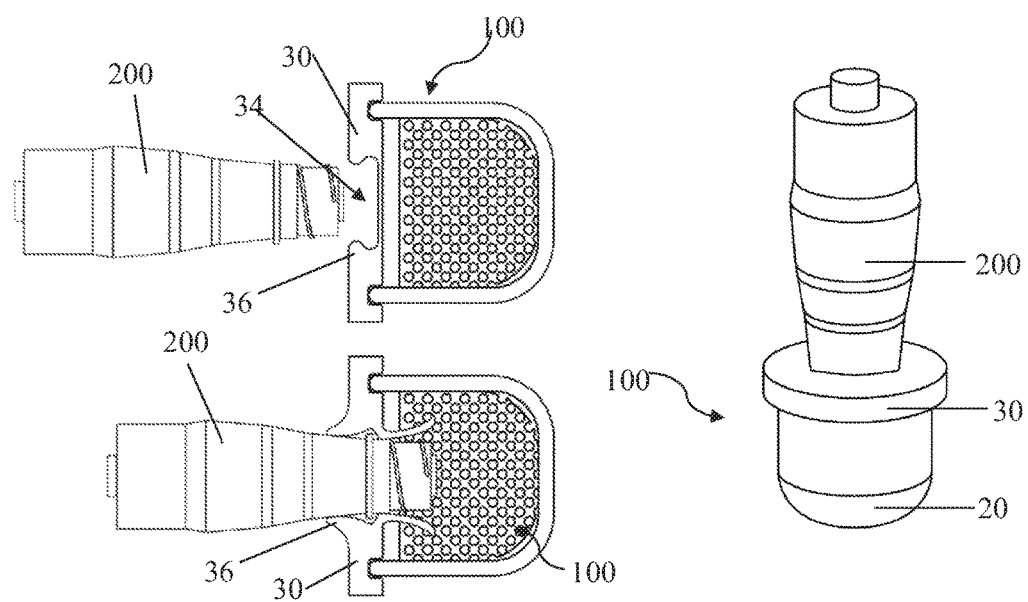
FIG. 21 illustrates a cross-sectional view of a device port being inserted into the device port cleaner for cleaning.
FIG. 22 illustrates a device port being inserted into an embodiment of the device port cleaner supported on its based.

As shown in FIGS. 21 and 22, the lip seals may enable the device port 200 to be supported by the device port cleaner 100 such that the device port 200 may be inserted into the device port cleaner 100 in any orientation without spillage. FIG. 21 shows that the device port 200 may be inserted into the device port cleaner 100 in a horizontal orientation. When inserted, the membrane 30 may support the device port 200 such that even when at a horizontal or an angled orientation, the device port 200 may not inadvertently lose contact with the cleaner 100. FIG. 22 shows that the base of the reservoir 20 may also comprise a flat bottom to support the cleaner 100 when the device port 200 is inserted in a vertical orientation. When the device port 200 is inserted into the device port cleaner 100 in a vertical orientation, the membrane 30 may hold the device port 200 in place as the device port cleaner 100 is set on its flat bottom.

Figures 19, 20:
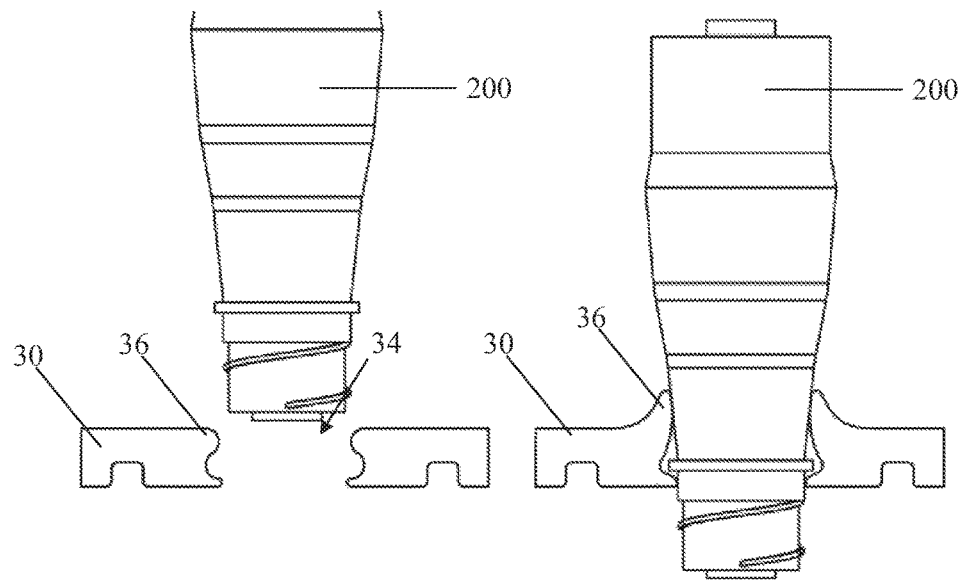
FIGS. 19 and 20 illustrate a cross-sectional view of a device port being inserted into another embodiment of the membrane of the device port cleaner.

When engaged with the device port cleaner 100, the device port 200 may be kept sterile and protected from microbes for up to seven days. Furthermore, in an alternative embodiment as shown in FIGS. 19-20, the lip seal formed by the upper lip ring 36 when the device port 200 is inserted may function regardless of the existence of the base 31 or the specific design of the slit 33 in the base 31. The elastic nature of the membrane 30 may allow for the device port cleaner 100 to be adaptable to the shapes and sizes of most medical device ports. Even without the base 31 or the complete rupture of the base 31 when the device port 200 is inserted such that there is no second lip seal formed by the base 31, the device port cleaner 100 may still successfully operate since the upper lip ring 36 may still form a lip seal with the device 200

Figure 23:
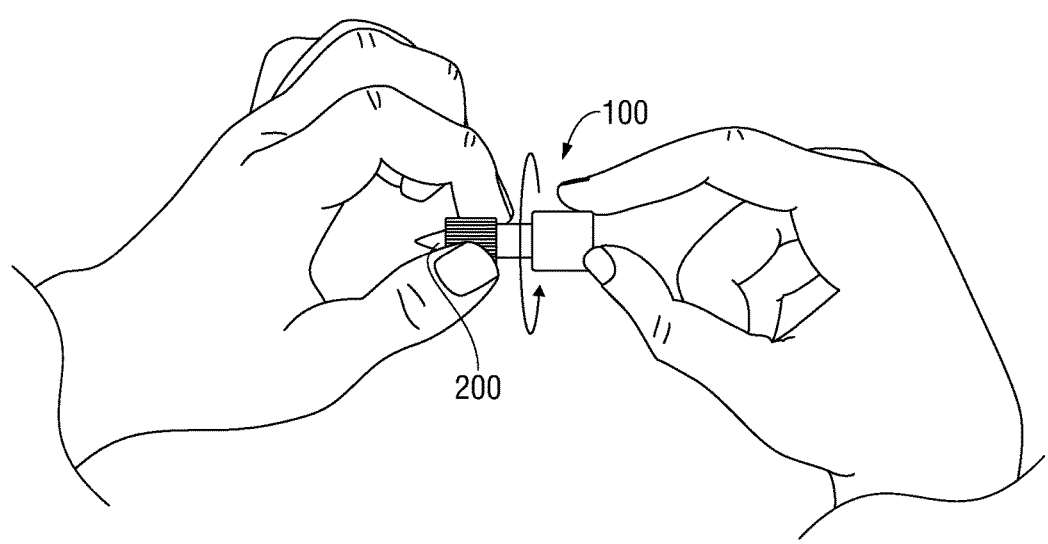
FIG. 23 illustrates a method of actively disinfecting a device port inserted in the device port cleaner by active manipulation.

Once the device port 200 penetrates the membrane 30 to access the reservoir 20, the device port 200 may be exposed to the disinfecting agent 40. Portions of the inserted device port 200 or the entire device port 200 may be inserted into the device port cleaner 100 for cleaning. The device port cleaner 100 may effectively wash both the inner and exterior surface of the device port 200 with the disinfecting agent 40, thereby cleaning surfaces not normally accessible by traditional cleaning methods. The disinfecting agent 40 may reduce and or eliminate microbial and or bacterial populations that may reside on any of the surfaces of the device port 200. As shown in FIG. 23, the inserted device port 200 may be further actively cleaned by physically manipulating at least one of the device port cleaner 100 or the device port 200 to agitate the disinfecting agent 40 over the immersed surfaces of the device port 200. A twisting motion of the device port 200 may be used to ensure complete exposure of all surfaces of the device port 200 needing to be cleaned.

Figure 24:
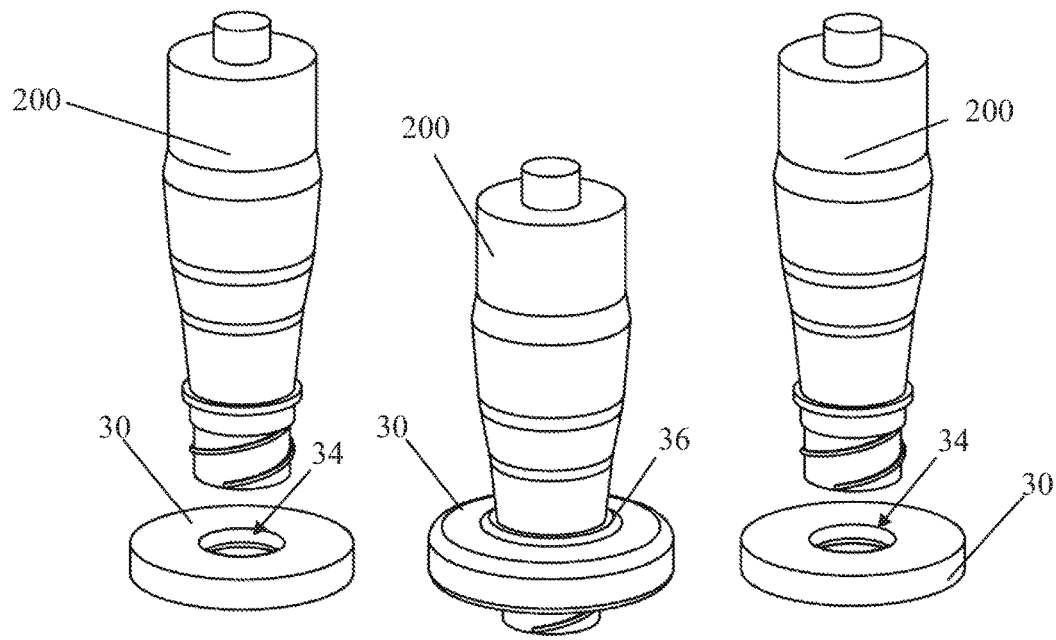
FIGS. 24 and 25 illustrate the device port being inserted into the device port cleaner and the membrane forming a lip seal around the inserted device port, respectively.
Figure 25:
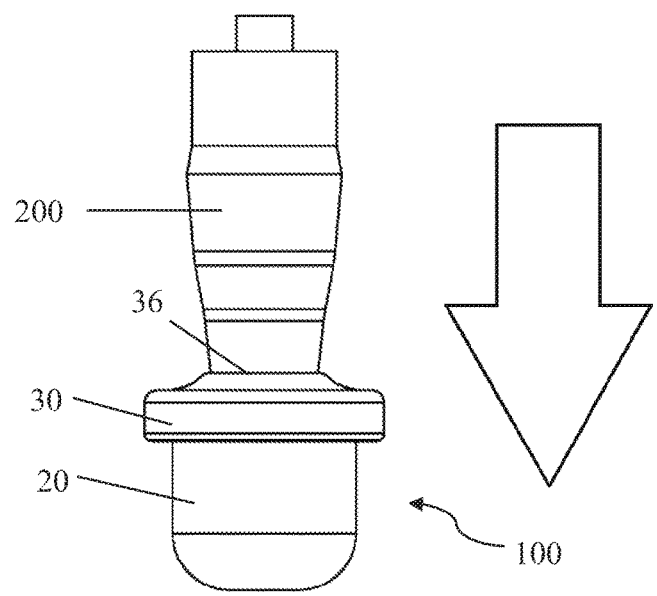

Turning to FIGS. 24-25, the membrane 30 may also be formed from a soft plastic or rubber based material such that when the device port 200 is inserted through the membrane 30, the upper lip ring 36 expands upon the entry of the port 200 to also create a lip seal. FIG. 24 shows that the elastic nature of the membrane 30 allows the membrane 30 to return to its original shape while maintain a sealed environment within the reservoir 20 during and after the device port 200 is withdrawn. The maintaining of the sealed and sterile environment after the device port 200 is withdrawn may enable the device port cleaner 100 to be used more than once.

Figure 26A:
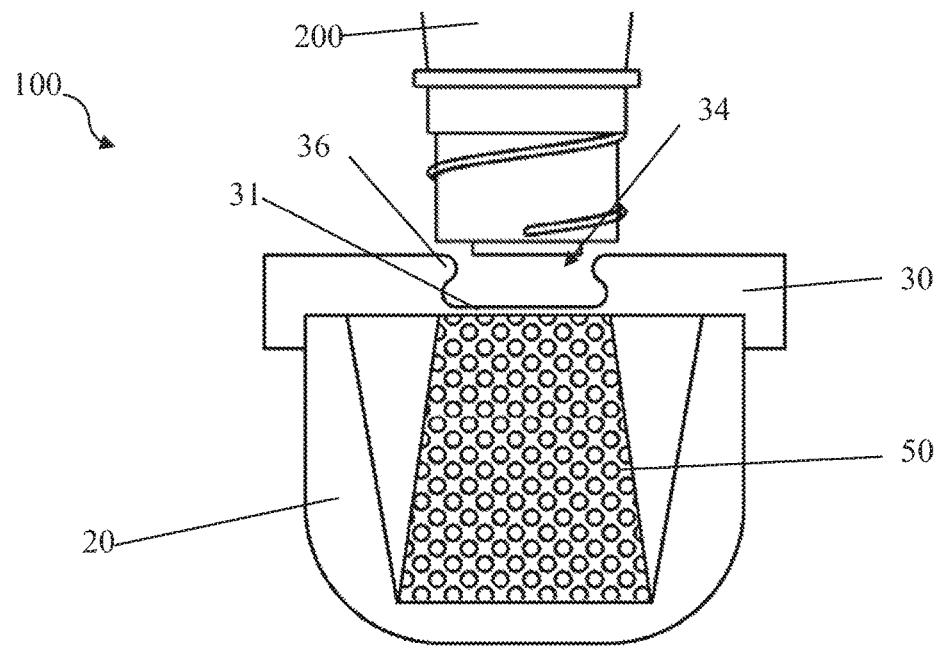
FIGS. 26A and 26B illustrates a device port being inserted into an embodiment of the device port cleaner with a release mechanism.
Figure 26B:
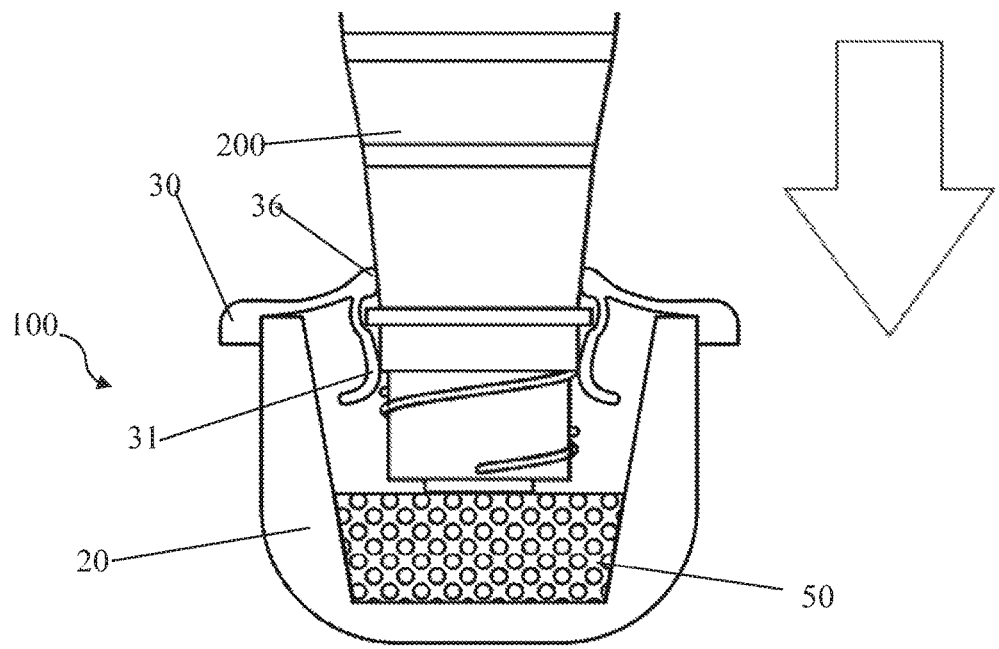

The device port cleaner 100 may further comprise a release mechanism 50 within the reservoir 20 for retaining and releasing the disinfecting agent 40. The release mechanism 50 may be used to retain the disinfecting agent 40 prior to the cleaner 100 being used. When the device port 200 is inserted into the device port cleaner 100, the release mechanism 50 may then release the disinfecting agent 40 to wash the inserted portion of the device port 200. As shown in FIGS. 26A and 26B, the release mechanism 50 may be engaged to dispense the disinfecting agent 40 as the device port 200 is inserted into the cleaner 100. In an embodiment, the release mechanism 50 may be an absorbent and compressible material. The release mechanism 50 may initially retain the disinfecting agent 40 by soaking up the disinfecting agent 40 prior to use. The release mechanism 50 or compressible material may then be compressed, releasing the disinfecting agent 40, as the device port 200 is inserted into the reservoir 20. Alternatively, the release mechanism may be coated in the disinfecting agent 40 or passively immersed in the disinfecting agent 40. The release mechanism 50 may be sized and shaped to closely fit within the reservoir 20 while still remaining compressible. Compression of the release mechanism 50 by the device port 200 as it is inserted into the cleaner 100, as shown in FIG. 26B, may dispense the disinfecting agent 40 retained by the release mechanism 50. The release mechanism 50 may be formed from an absorbent, porous, and compressible material including but not limited to a sponge, absorbent cotton, polyurethane, polyvinyl alcohol, silicone, cellulose wood fibers, foam, foamed plastic polymers, and the like.

Figure 27A:
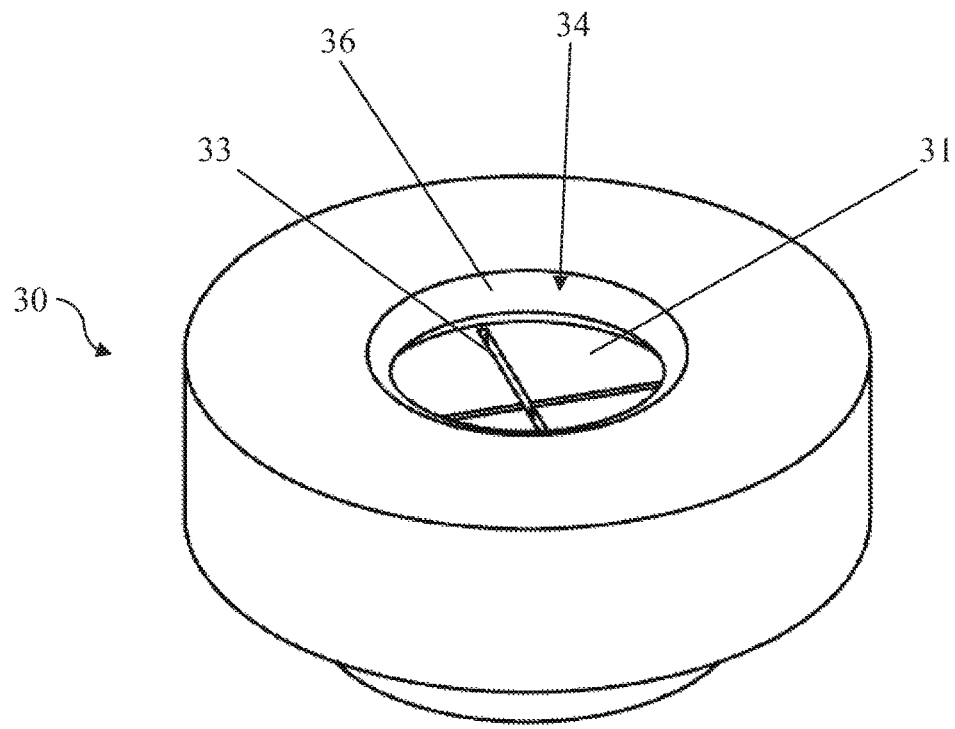
FIGS. 27A and 27B illustrate an embodiment of the membrane with a threaded portion.
Figure 27B:
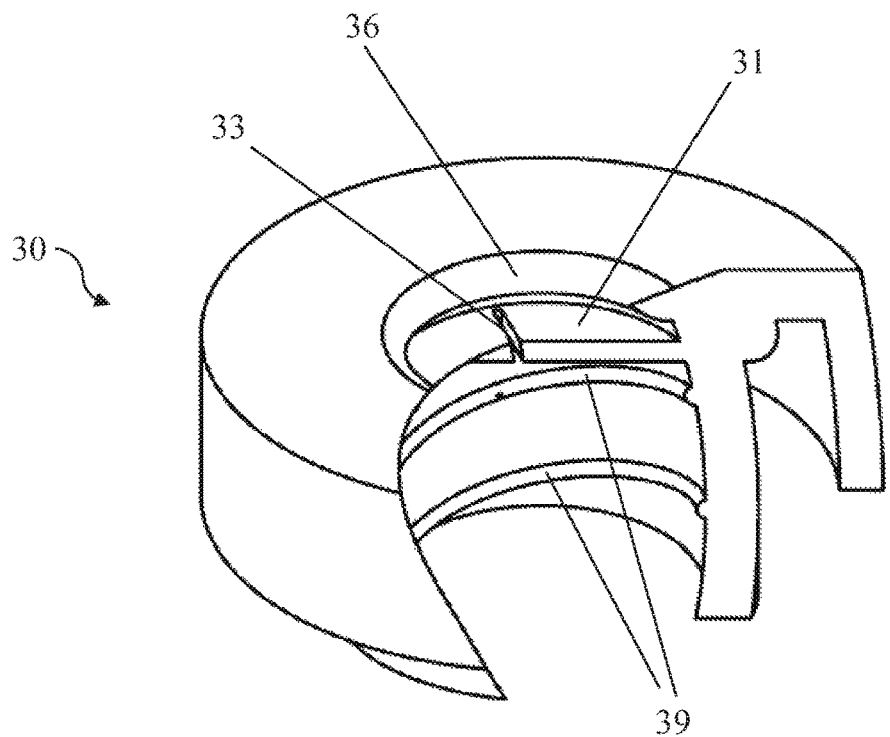

In an alternate embodiment, the membrane 30 may further comprise an internal threading 39 for inserting the device port 200 into the device cleaner 100. Once the device port 200 penetrates the base 31 in the membrane 30, the device port 200 may be threaded into the device port cleaner 100. As shown in FIGS. 27A and 27B, the internal threading 39 may be adjacent to the membrane 30 below the bulb cavity 34. After penetrating the slits 33 of the base 31 in the membrane 30, the device port 200 may be threaded into the internal threading 39 to fasten and secure the port 200.

Alternatively, the device port 200 may be threaded into the membrane 30 prior to penetrating the base 31. The penetrated slits 33 in base 31 may maintain a tight and close-fit seal around the external surface of the inserted device port 200 as the device port 200 is being threaded into the device port cleaner 100. The internal threading 39 may further secure the positioning of the inserted device port 200 and prevent inadvertent withdrawal of the port 200 prior to use, thereby increasing the risk of being re-contaminated. The upper lip ring 36 and the base 31 of the membrane 30 may both still form a lip seal around the device port 200 after insertion. The internal threading 39 and the membrane 30 may be of a single component and may be formed as a single unitary construction. Alternatively, the threading 39 and the membrane 30 may be more than one components assembled, fitted, or bonded together.

Figures 28A, 28B, 28C:
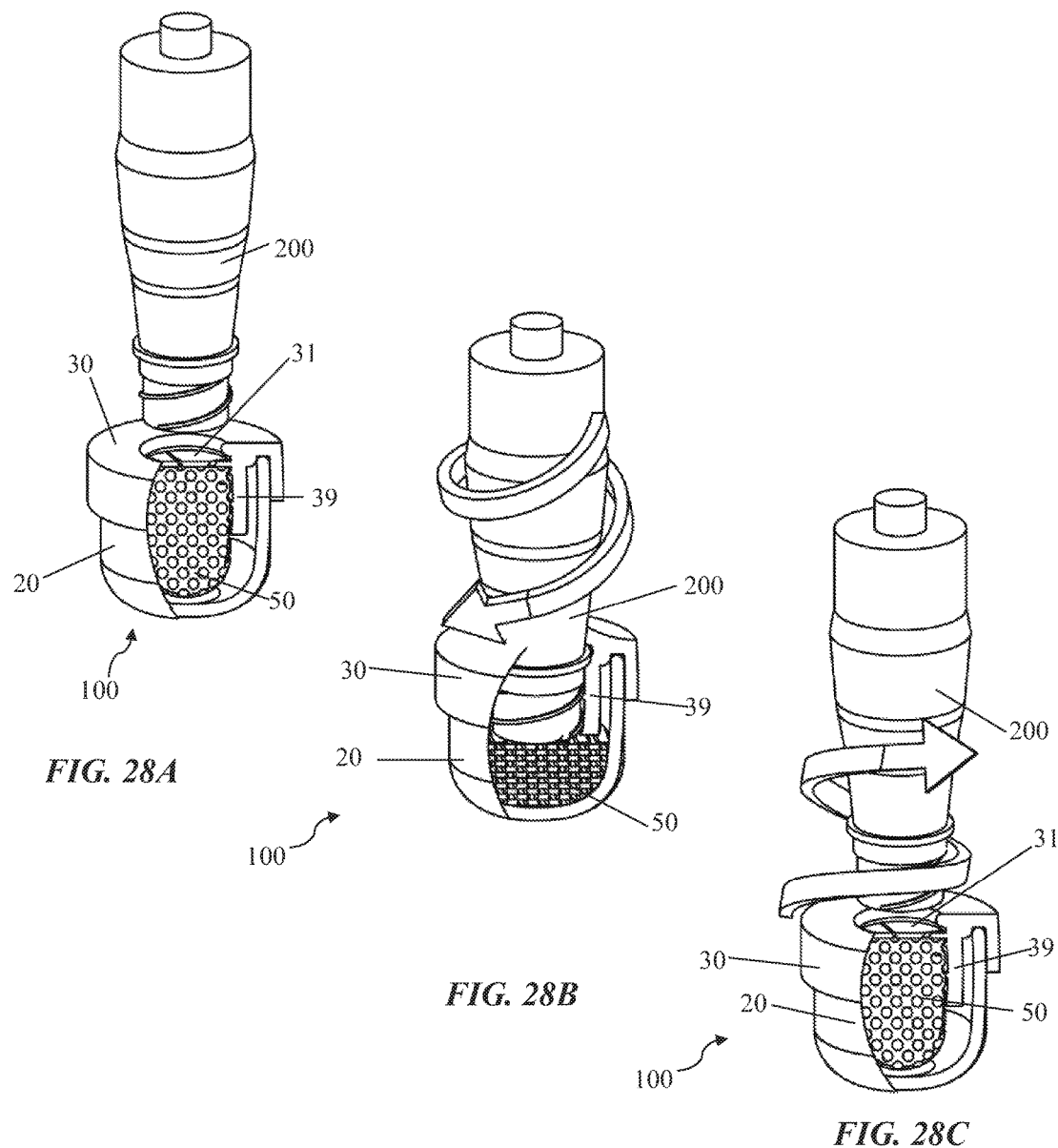
FIGS. 28A-28C illustrate the port device being threaded into the device port cleaner.

FIGS. 28A-28C show a device port 200 being threaded into an alternative embodiment of the device port cleaner 100. After the port 200 penetrates the membrane 30, the device port 200 may be further secured in the cleaner 100 by being threaded into the internal threads 39 of the device port cleaner 100. As the device port 200 is being threaded into the cleaner 100, FIG. 28B shows the device port 200 compressing against the release mechanism 50. The compression of the release mechanism 50 may release the device port 200 to the disinfecting agent 40. The threading of the device port 200 may aid in compressing the release mechanism 50 since it allows for the gradual and controlled compression of the release mechanism 50, as well as provide support against any push back from the compressed release mechanism 50 against the inserted port 200. The internal threading 39 may also act as a retainer in keeping the device port 200 and the device port cleaner 100 engaged until the cleaner 100 is purposefully removed. FIG. 28C shows that when the device port 200 is un-threaded and removed, the membrane 30 including the slits 33 and the release mechanism 50 may all return to their original positions.

Figures 29A, 29B, 29C:
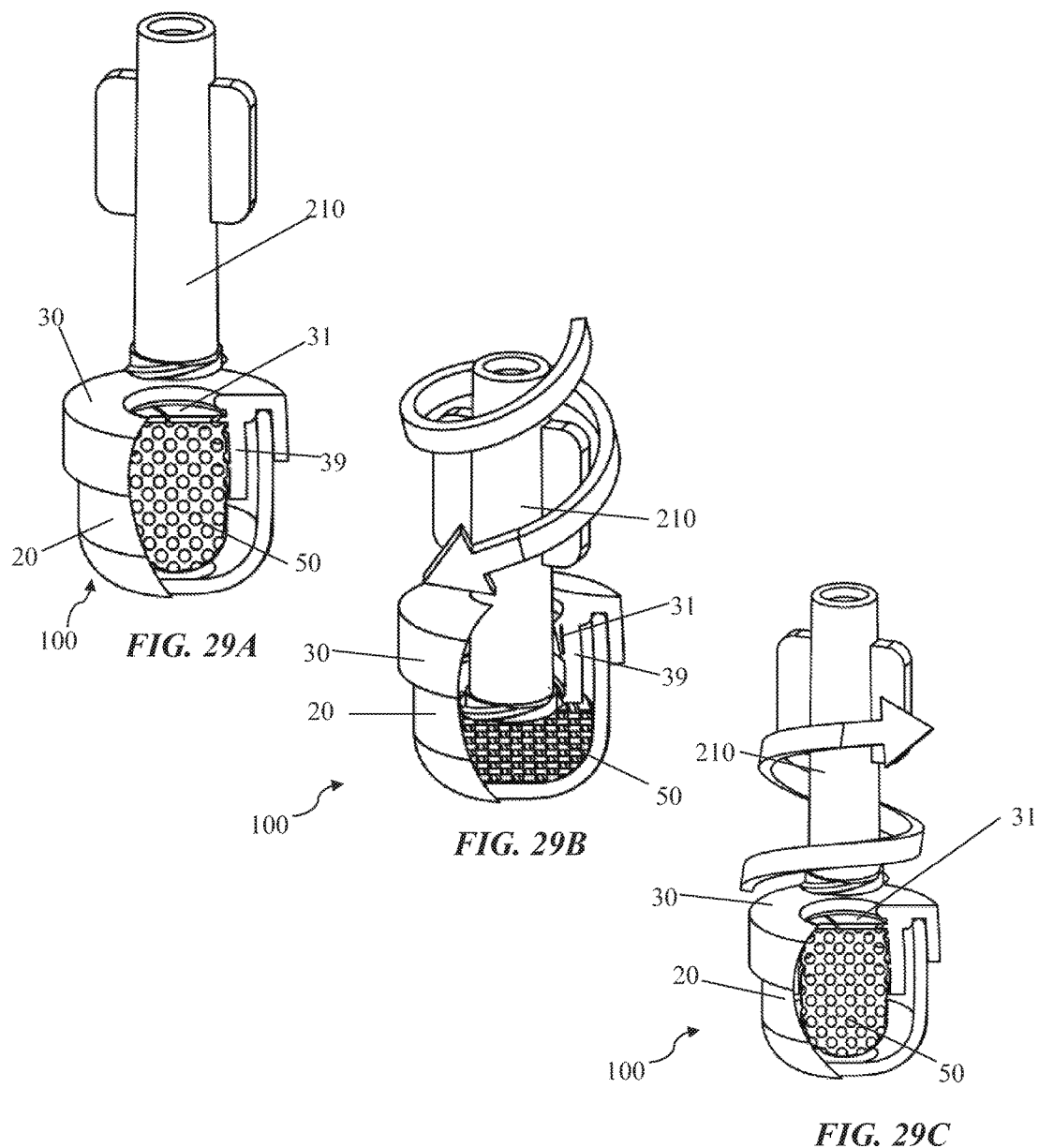
FIGS. 29A-29C illustrate a female port being threaded into the device port cleaner.
Figure 30:
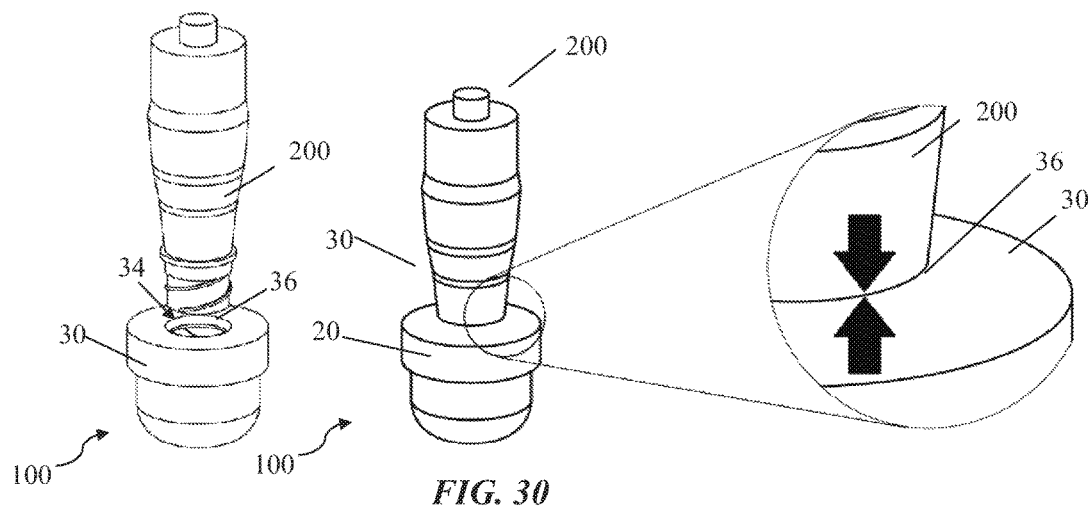
FIG. 30 illustrates a zero clearance lip seal between the membrane and the inserted port device.
Figure 31:
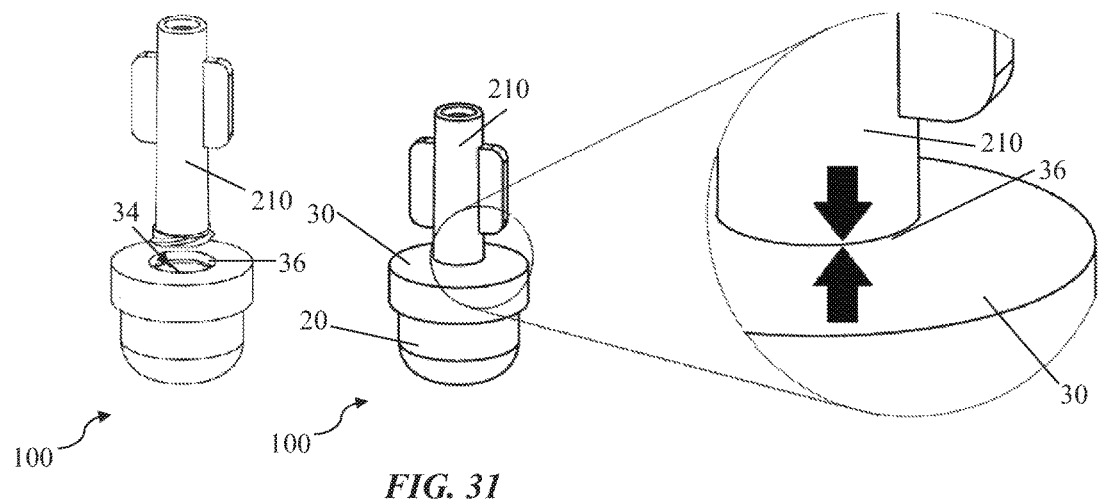
FIG. 31 illustrates a zero clearance lip seal between the membrane and the inserted female port.

The lip seals formed between the membrane 30 and the inserted device port 200, in conjunction with the internal threading 29 in the membrane 30, may still permit the use of the device port cleaner 100 with different device ports of varying diameters. As an example of the adaptive nature of the cleaner 100, the device port cleaner 100 may also be used with thinner device ports such as a needle port 210, as shown in FIGS. 29A-29C. The needle port 210 may be inserted into the device port cleaner 100 as it is penetrated through the membrane 30 and then threaded with the internal skirt 39. The lip seal formed by the slits 33 in the membrane 30 may adapt to the thinner diameter of the body of the needle port 210 to seal the interior of the reservoir 20 from contaminants. As the needle port 210 is threaded into the reservoir 20 of the cleaner 100, the needle port 210 may compress the release mechanism 50 to release the disinfecting agent 40. The disinfecting agent may sterilize and clean the inserted portion of the needle port 210. FIGS. 30 and 31 show that regardless of the diameter of the inserted device port, the lip seal produced by the slit 33 in the membrane 30 may ensure a "zero clearance" seal between the membrane 30 and both the device port 200 or the needle port 210.

Figure 32:
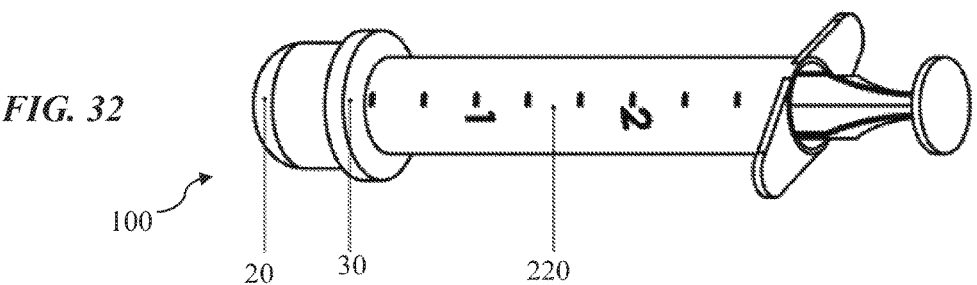
FIGS. 32 and 33 illustrate the device port cleaner being used to clean a medical syringe.
Figure 34:
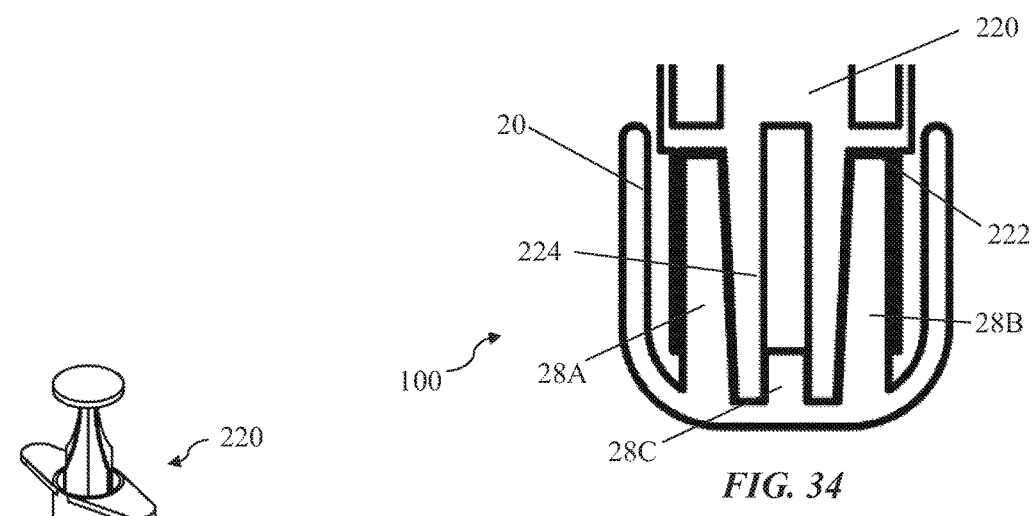
FIG. 34 illustrates a cross-sectional view of an embodiment of the device port cleaner with additional internal protrusions cleaning the inner and outer surfaces of an inserted medical syringe.
Figure 33:
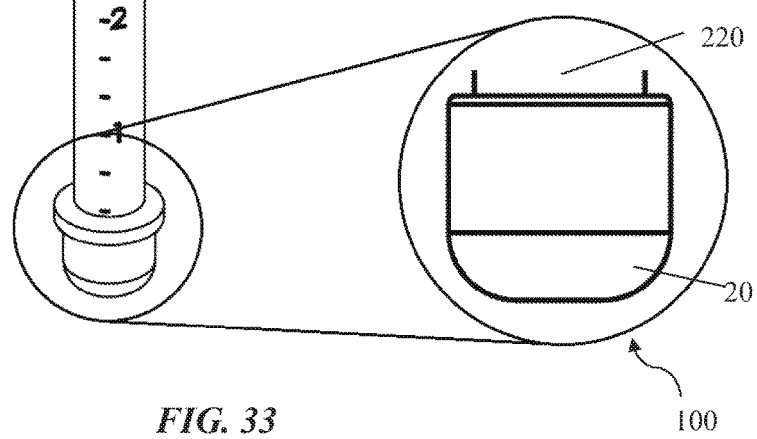

The device port cleaner 100 may also be used to clean the male/female end of a medical syringe 220. As shown in FIGS. 32 and 33, the male/female connecting end of the medical syringe 220 may be similarly inserted into the device port cleaner 100 for cleaning. The device port cleaner 100 may clean both the inner and outer surfaces of a connecting end 224 of the medical syringe 220 when inserted into the device port cleaner 100. In an embodiment, as shown in FIG. 34, the reservoir 20 may further comprise internal protrusions 28A-28C to accommodate for the geometry of the inserted connecting end 224 of the medical syringe 220. The protrusion 28C may clean the internal thread skirt of the medical syringe 220. The larger protrusions 28A, 28B may clean the conical fitting area 222 of the medical syringe 220. The shape, size, quantity, and design of the protrusions within the reservoir 20, as well as the reservoir 20 itself, may be adapted to accommodate for the various geometry and shapes of different connecting ends of both the device port 200 and the medical syringe 220.

Figure 35:
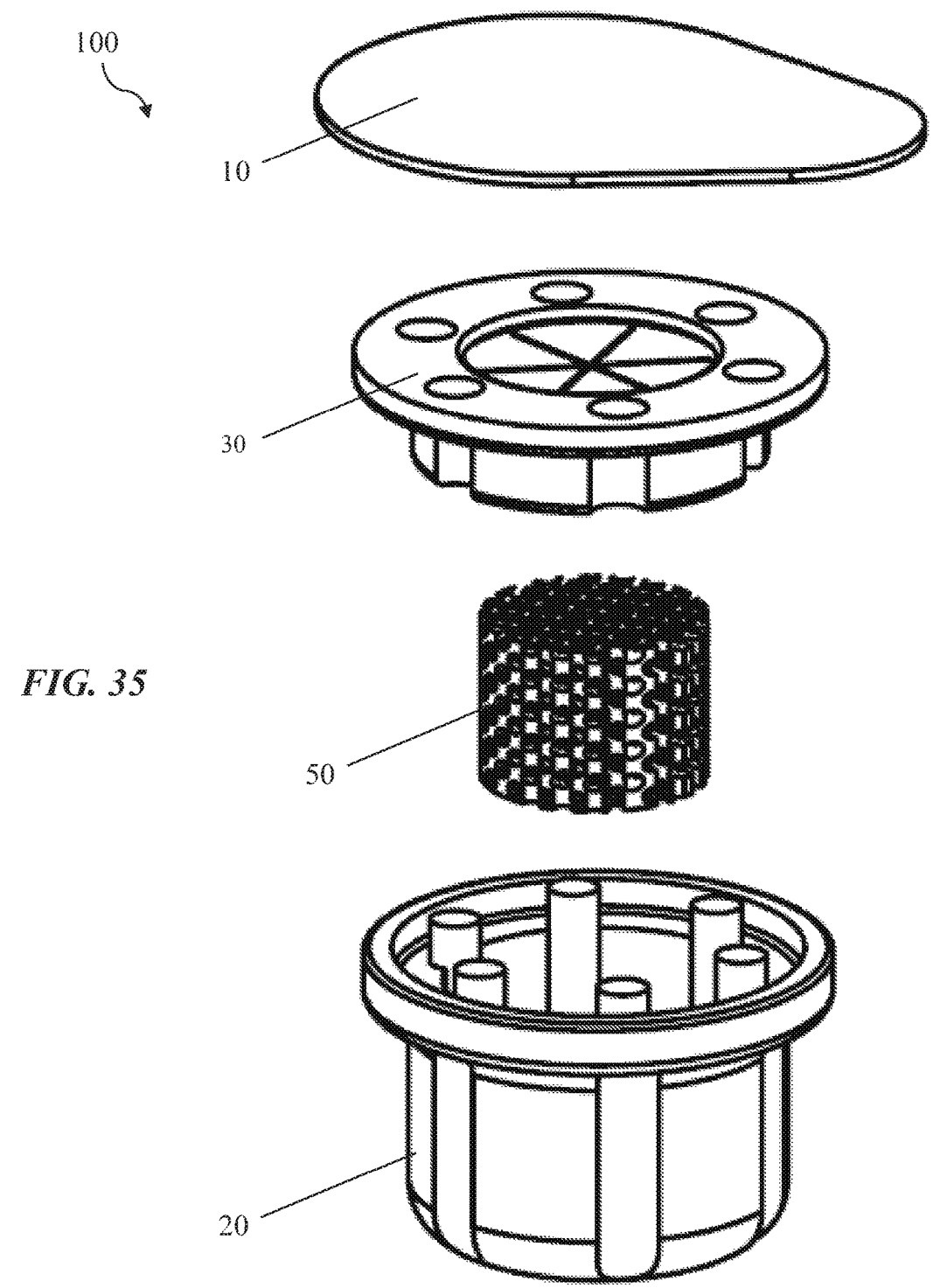
FIG. 35 illustrates an exploded view of yet an additional embodiment of the device port cleaner.
Figure 36:
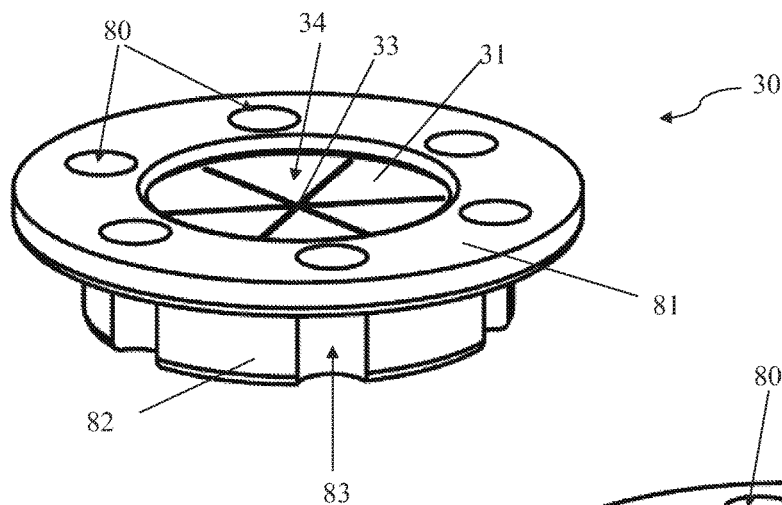
FIGS. 36 and 37 illustrate a perspective and sectional view, respectively, of an additional embodiment of the membrane with a membrane flange, a membrane perforation, and a membrane groove.
Figure 37:
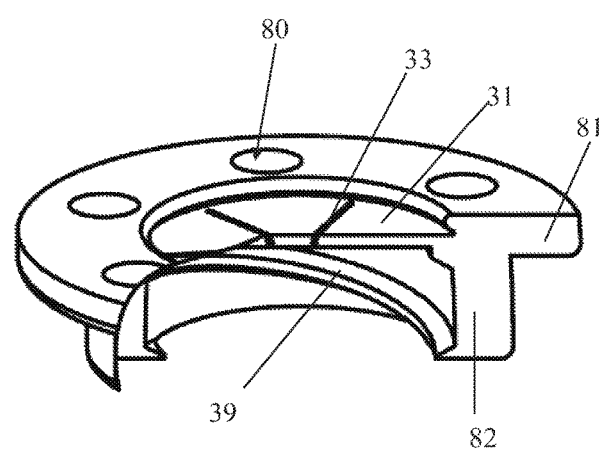

Turning to FIG. 35, another embodiment of the device port 100 is shown with the device port 100 further comprising additional features on the membrane 30 and reservoir 20. As shown in FIGS. 36 and 37, in an embodiment, the membrane 30 may further comprise a membrane flange 81 containing a series of membrane perforations 80, a membrane body 82, and a series of membrane grooves 83 formed into the exterior surface of the membrane body 82. The membrane flange 81 may be formed around the bulb cavity 34 and extend circumferentially outwards pass the outer surface of the membrane body 82. The membrane body 82 may extend downwards from the membrane flange 81 like a hollow cylinder with the interior surface of the membrane body 82 approximately outlining the bulb cavity 34. The membrane body 82 may extend outwards from the membrane flange 81 in the direction towards the interior of reservoir 20 when the membrane 30 is coupled to the reservoir 20 during assembly. The membrane flange 81 may further comprise a series of membrane perforations 80 formed into the membrane flange 81. Each of the membrane perforations 80 may be formed in the shape of a circular cutout as shown in FIGS. 36 and 37. Alternatively, the membrane perforations 80 may be any other shape or size such as oval, triangular, square, quadrilateral, and the like. The membrane perforations 80 may be arranged concentrically around the bulb cavity 34 each equal distant from the bulb cavity 34.

The membrane perforations 80 may extend from the top surface of the membrane flange 81 through the entirety of the membrane flange 81 and membrane body 82. The membrane body 82 may be of various thicknesses such that the extrusion of the membrane perforations 80 may partially cut through the membrane body 82 to form the membrane grooves 83, as seen in FIG. 36. Since the membrane grooves 83 are formed by the extension of the membrane perforations 80 through the membrane body 82, the number, shape, size, and position of each the membrane grooves 83 may match the number, shape, size, and position of each of the concentrically placed membrane perforations 80. The maximum width of membrane grooves 83 formed by the extrusion of the membrane perforations 80 may also match the diameter of each of the membrane perforations 80. The membrane body 82 may be of various thicknesses. The membrane perforation 80 may be of various diameters. In the instance that the outer surface of the membrane body 82 from the bulb cavity 34 does not extend pass or intercept the placement and opening of the membrane perforations 80, there may not be any membrane grooves 83 formed in the membrane body 82. In the instance that the outer surface of the membrane body 82 extends pass the entirety of the membrane perforation 82, cylindrical cutouts, instead of the membrane grooves 83, may be extruded through the entire membrane body 82 at each of the membrane perforations 82. The sectional view of the membrane 30 in FIG. 37 shows the base 31 of the bulb cavity 34 with slits 33, and the interior surface of the membrane body 82 with the threading 39. The threading 39 spirals along the interior surfaces of the membrane body 82. The threading 39 begins where the membrane body 92 extends from the membrane flange 81 near the bottom surface of the base 31, and extends towards the base of the membrane body 82.

Figure 38:
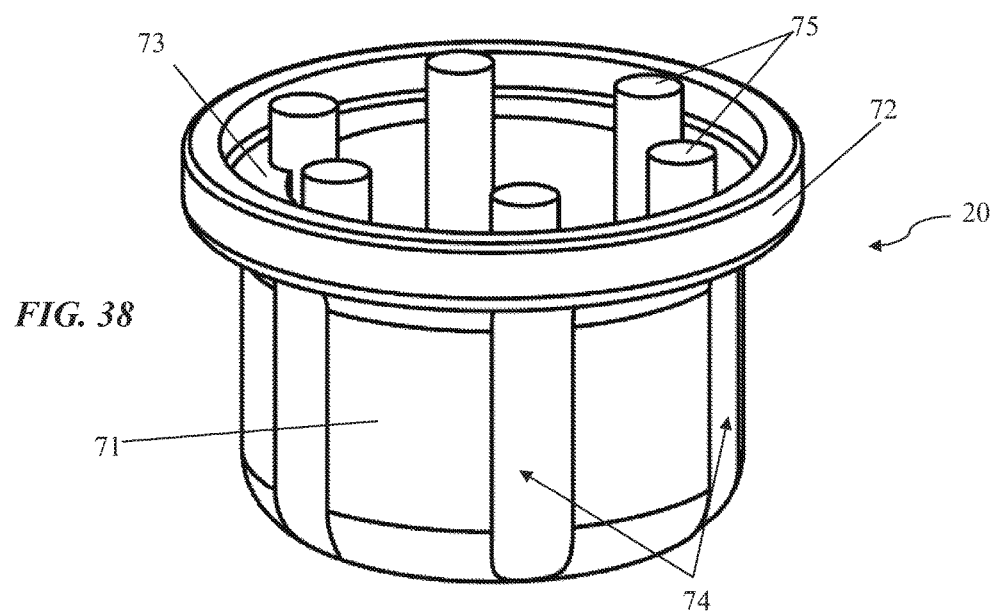
FIG. 38 illustrates a perspective view of an additional embodiment of the reservoir with a reservoir flange, a reservoir extrusion, and a reservoir groove.

Turning to FIG. 38, in an embodiment, the reservoir 20 may further comprise a reservoir body 71 with reservoir grooves 74, a reservoir flange 73, and a reservoir ring 72. The reservoir flange 73 may be formed along the opening end of the reservoir 20 and extend outwards away from the interior of the reservoir 20. From the top surface of the reservoir flange 73, the reservoir ring 72 may be initially formed along the outer circumference of the reservoir flange 74 and further extend in the direction of the opening of reservoir 20. The extension of the reservoir ring 72 may increase the overall height of the walls of the reservoir 20. Along the interior surface of the reservoir body 71, the reservoir 20 may further comprise a series of reservoir extrusions 75 extending out of the opening of the reservoir 20 through the interior opening of the reservoir flange 73 and the reservoir ring 72. The reservoir extrusions 75 may be formed in the shape of a series of concentric cylindrical tubes extending out of the interior of the reservoir 20. The reservoir body 71 may further comprise a series of reservoir grooves 74 formed in the outer surface of the reservoir body 71. The reservoir grooves 74 may extend from the base of the reservoir body 71 towards the reservoir flange 73. The reservoir grooves 74 may be of various width, length, depth, and number subject to the preference of the user or manufacturer. The reservoir grooves 74 may function to provide a grip for handling the device port cleaner 100.

The reservoir extrusions 75 are provided to mate with the membrane perforations 80 as the membrane 30 is coupled to the reservoir 20 by being secured over the opening 22. As such, the position, size, shape, and number of reservoir extrusions 75 may match the corresponding features of the membrane perforations 80, respectively. The ends of the reservoir extrusions 75 may be sized to be just slightly smaller than the membrane perforations 80 such that the reservoir extrusions 75 may snuggly fit through each of the corresponding membrane perforations 80. Alternatively, each of the reservoir extrusions 75 may be designed and formed such that when the reservoir extrusion 75 is mated with the membrane perforation 80, the portion of the reservoir extrusion 75 protruding out of the top surface of the membrane flange 81 is bucked to the membrane 30 like a rivet, permanently bonding the membrane 30 to the reservoir 20. The reservoir extrusion 75 and the corresponding rivet that may be formed when connected to the membrane 30 may be of various size and shapes such as circular, oval, and the like.

Figure 39A:
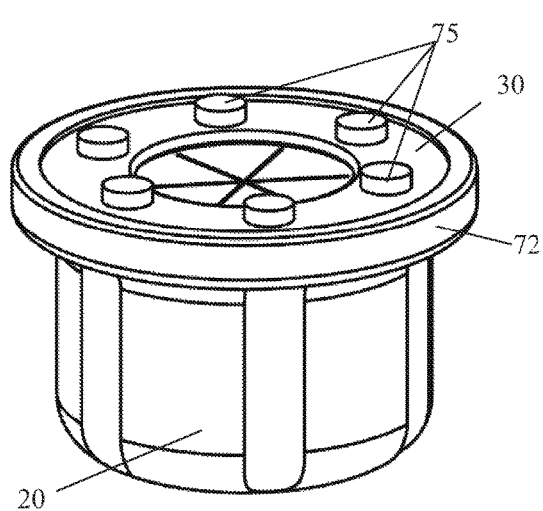
FIGS. 39A and 39B illustrate an embodiment of the membrane having the membrane flange coupled to the reservoir having the reservoir groove.
Figure 39B:
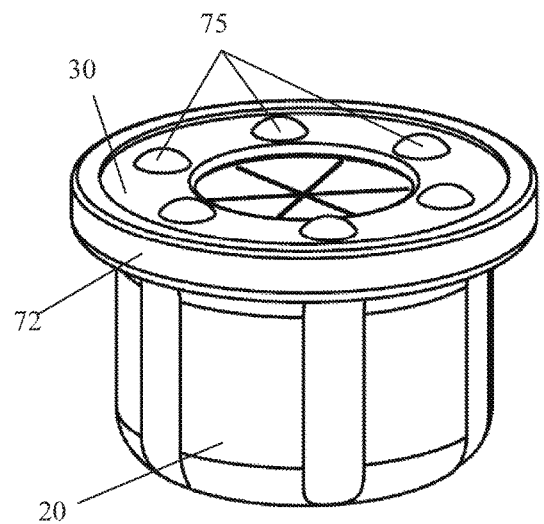

Turning to FIGS. 39A and 39B, the membrane 30 shown in FIG. 36 may be coupled to the reservoir 20, as shown in FIG. 38, by fitting the entirety of the membrane 30 within the reservoir ring 72. The membrane 30 may be positioned within the reservoir ring 72 to cover and seal the opening 22 of reservoir 20. The membrane 30 may couple with the reservoir 20 such that the bottom surface of the membrane flange 81 contacts the top surface of the reservoir flange 73. The fitting of the membrane 30 over the reservoir 20 in the instant embodiment may also require that the protruding ends of each of the reservoir extrusion 75 be aligned with a corresponding membrane perforation 80. When aligned, each of the reservoir extrusion 75 may be positioned to extend through a respective membrane groove 83 and membrane perforation 80 as the membrane 30 is fitted against the reservoir flange 73. When the membrane 30 is fitted within the reservoir ring 72 and covering the opening 22 of reservoir 20, as shown in FIGS. 39A and 39B, the outer surface of the membrane 82 may be contacted against the interior surfaces of the reservoir body 71. The height of the reservoir ring 72 may be formed to be taller than the thickness of the membrane flange 81 such that when the membrane 30 is fitted within the reservoir ring 72 and the membrane flange 81 is brought in contact with the reservoir flange 73, the top surface of the membrane flange 81 is positioned lower than the top surface of the reservoir ring 73 inside the interior of the reservoir 20. When the membrane 30 is fitted against the reservoir flange 73, each of the aligned reservoir extrusion 75 may extend out of a respective membrane perforation 80 such that the extrusion 75 protrudes pass the top surface of the membrane 30. In FIG. 39B, an alternative embodiment is shown wherein once the membrane 30 is coupled to the reservoir 20 with each of the reservoir extrusion 75 mated through a respective membrane perforation 80, the protruding portion of the reservoir extrusion 75 may buck over the top surface of the membrane 30 like a rivet, permanently bonding the membrane 30 to the reservoir 20.

Figure 40:
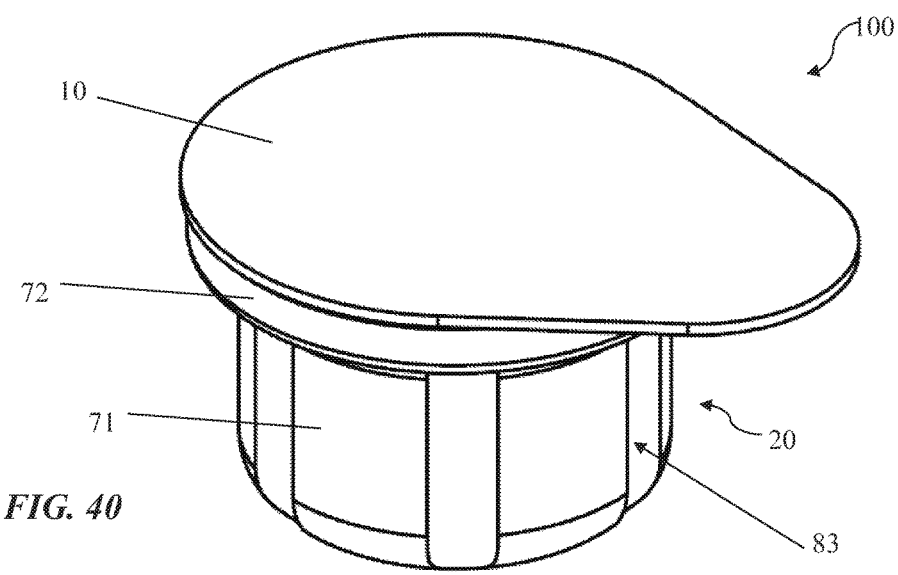
FIG. 40 illustrates the reservoir having the reservoir groove sealed with the lid.

FIG. 40 shows an embodiment of an assembled device port cleaner 100 with the lid 10 sealed against the top surface of the reservoir ring 72. The recession between the top surface of the membrane flange 81 and the top surface of the reservoir ring 72, once the membrane 30 is fitted over the opening 22 of the reservoir 20, may allow the lid 10 to completely seal the membrane 30 and the interior of the reservoir 20 from the external environment. When sealed, only the outer surface of the reservoir 20 and the lid 10 may be exposed to the external environment. This allows the interior of the reservoir 20, the release mechanism 50, the disinfecting agent 40, and the membrane 30 to remain isolated within the device port cleaner 100 in sterile conditions. In the embodiment shown, the lid 10 may comprise an induction foil seal that may be peeled off from the reservoir ring 72 prior to using the device port cleaner 100. The lid 10 may further comprise a foil lid liner. Alternatively, the lid 10 may be made of other materials including aluminum paper, aluminum polymer, polymer, nylon, and the like.

Figure 41A:
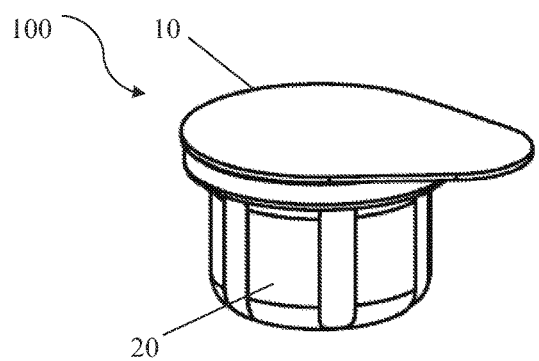
FIGS. 41A-41D illustrate an embodiment of the device port cleaner with the membrane having the membrane flange and the reservoir having the reservoir groove being used to clean the device port.
Figure 41B:
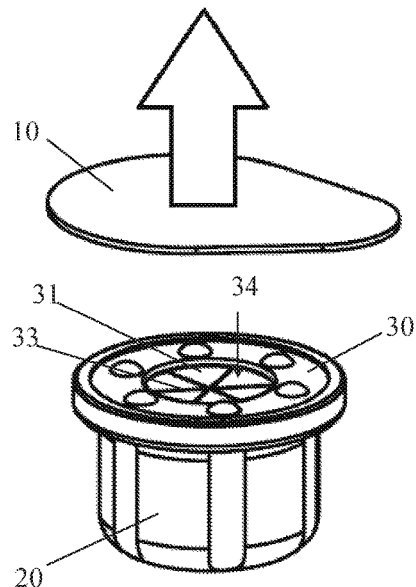
Figure 41C:
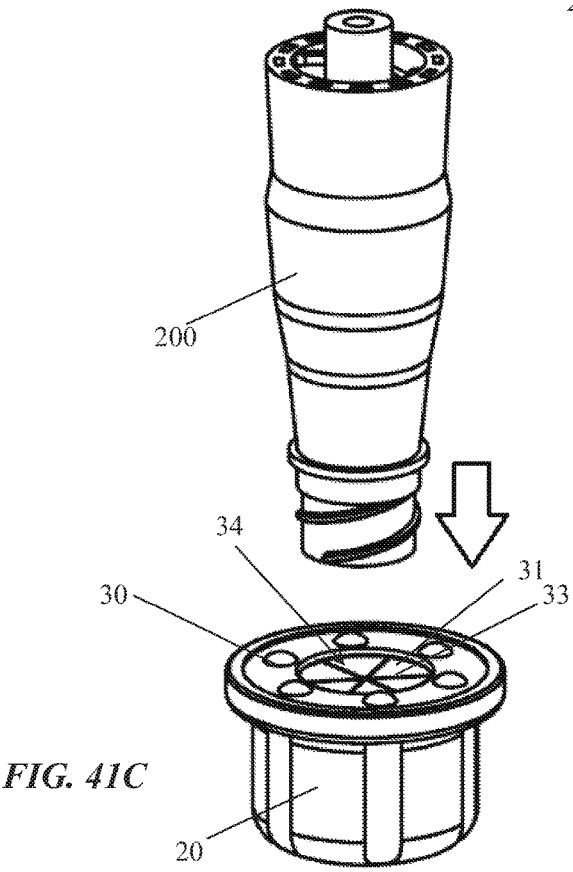
Figure 41D:
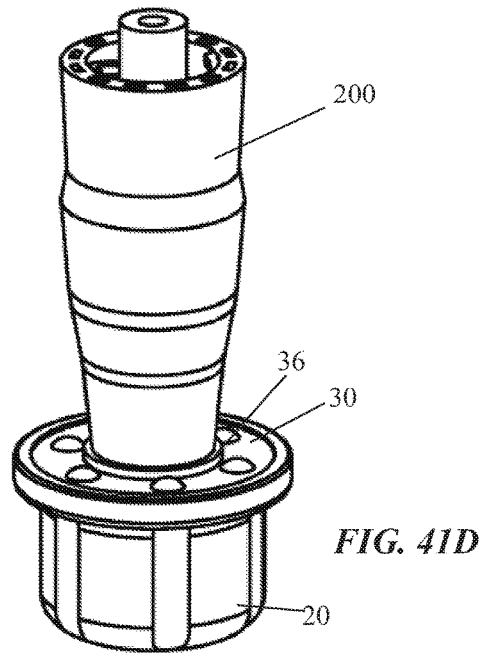

FIGS. 41A-41D show in an embodiment, a method of using the device port cleaner 100 shown in FIG. 41A to clean the device port 200. Before using the device port cleaner 100, the lid 10 may first be peeled off or removed, as shown in FIG. 41B, to expose the top surface of the membrane 30 and the bulb cavity 34. In FIG. 31C, the end of the device port 200 needing to be cleaned may then be brought in alignment with the bulb cavity 34 in the membrane 30. The bulb cavity 34 is where the device port 200 may penetrate the membrane 30 as the device port 200 is inserted into the reservoir 20 for cleaning. The device port 200 may penetrate the membrane 30 by being inserted through the slits 33 in the base 31 of the bulb cavity 34. As the device port 200 is inserted into the reservoir 20 through the membrane 30, the upper lip ring 36 of the bulb cavity 34 may conform to the shape of the outer circumference of the device port 200 and form a lip seal against the device port 200, as shown FIG. 41D.

Figure 42:
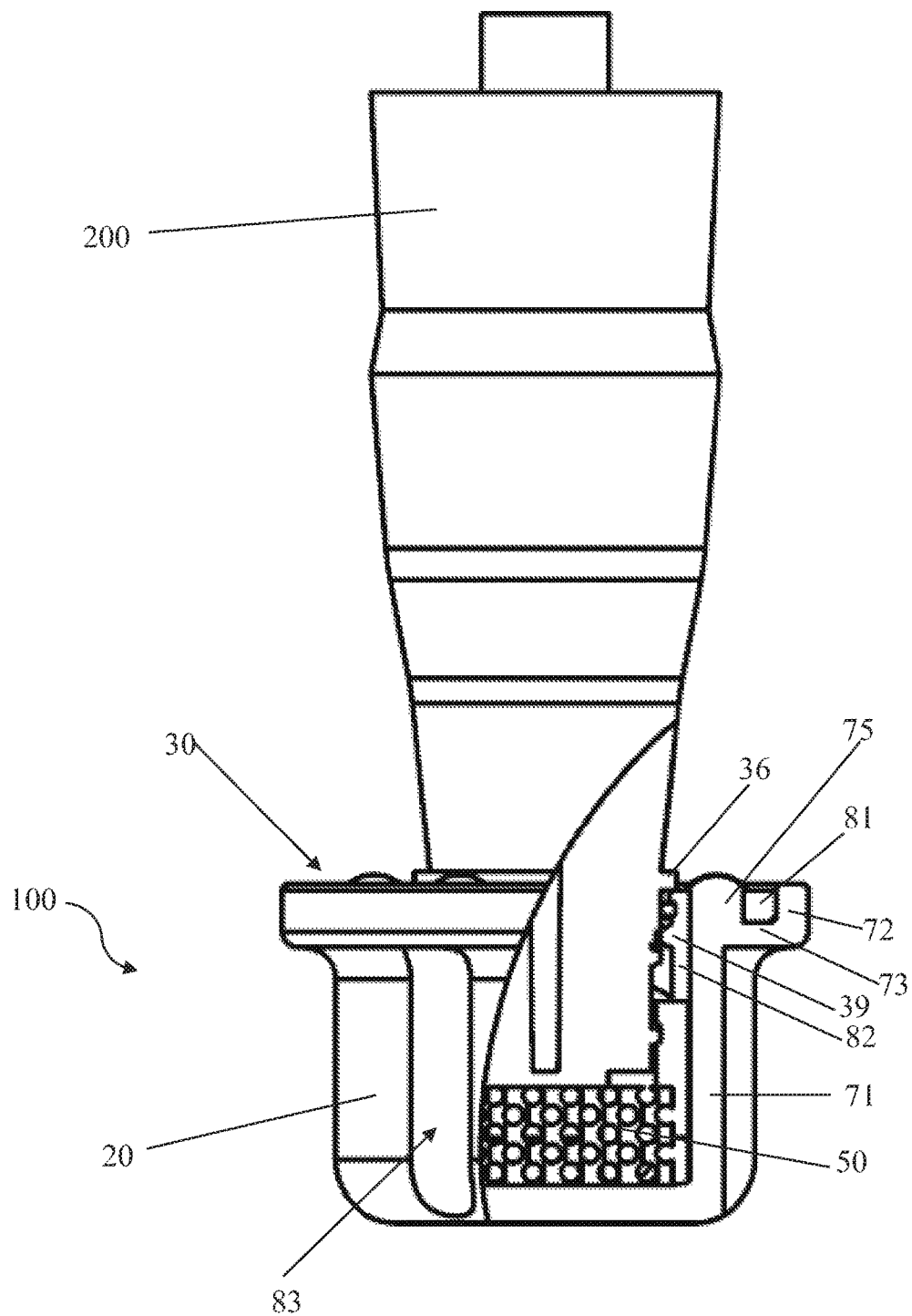
FIG. 42 illustrates a sectional view of the device port inserted through the membrane having the membrane flange into the reservoir having the reservoir groove.

The sectional view of the device port 200 inserted into the device port cleaner 100 in FIG. 42 shows that the device port 200 compressing the release mechanism 50 as it is inserted. The release mechanism 50 may hold a disinfecting agent 40 that may be released as the release mechanism 50 is compressed by the device port 200. Alternatively, the reservoir 20 may only contain a disinfecting agent 40 without the release mechanism 50 wherein the device port 200 may be exposed to the disinfecting agent 40 directly as it is inserted into the device port cleaner 100.

Figure 43:
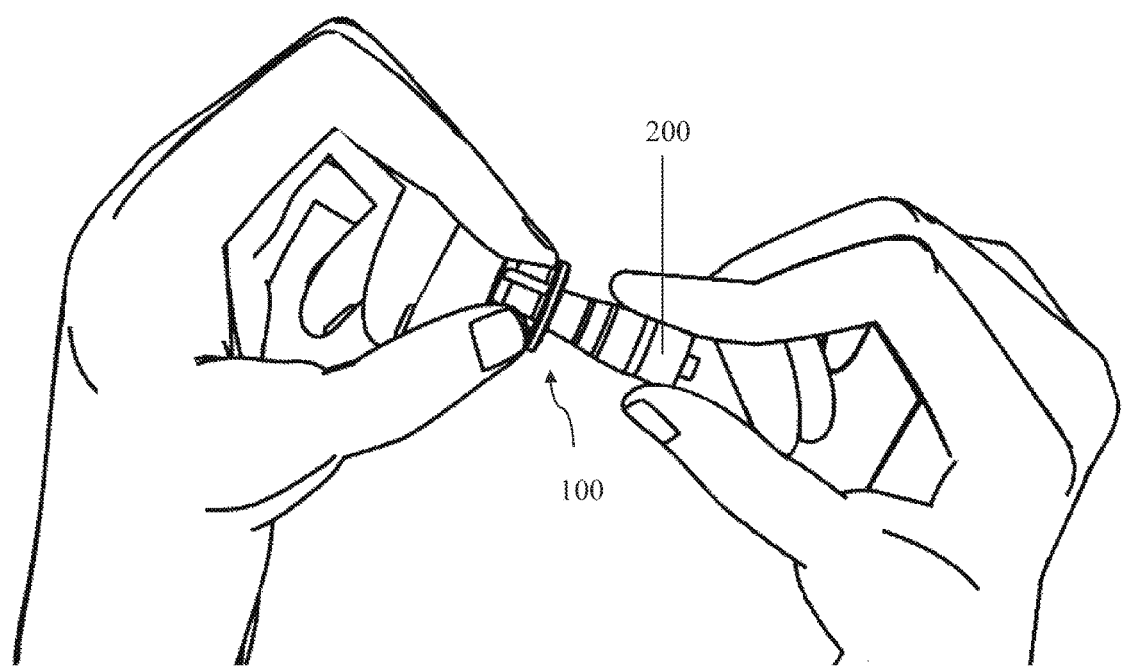
FIG. 43 illustrates a method of inserting the device port into the device port cleaner by gripping the reservoir grooves on the reservoir of the device port cleaner.

FIG. 42 also shows the device port 200 being inserted by being threaded into the device port cleaner 100. The device port 200 may be threaded against the threading 39 along the interior of the membrane body 82 to secure the device port 200. The threading of the device port 200 into the device port cleaner 100 may ensure a secure contact with the device port cleaner 100, prevent the inadvertent withdrawal and subsequent contamination of the device port 100, and prevent spillage of the interior contents of the reservoir 20. FIG. 43 shows a user threading the device port 200 into the device port cleaner 100 by gripping the reservoir grooves 74 in the reservoir body 20. The reservoir grooves 74 provides grip for handling the device port cleaner 100 and may reduce the risk of accidentally dropping the device port cleaner 100 while handling it.

Having thus described the present invention by reference to certain of its exemplary embodiments, it is noted that the embodiments disclosed are illustrative rather than limiting in nature and that a wide range of variations, modifications, changes, and substitutions are contemplated in the foregoing disclosure and, in some instances, some features of the present invention may be employed without a corresponding use of the other features. Many such variations and modifications may be considered desirable by those skilled in the art based upon a review of the foregoing description of exemplary embodiments. Accordingly, it is appropriate that any claims supported by this description be construed broadly and in a manner consistent with the scope of the invention.

We claim:

1. A device cleaner for cleaning an end of a device port, comprising:
 a hollow body with an opening;
 a disinfecting agent within the hollow body;
 a membrane covering the opening of the hollow body, wherein the membrane creates a seal within the hollow body prior to the membrane being penetrated by at least a portion of a device port inserted within the hollow body;
 wherein the membrane is configured to be penetrable by the device port to provide the at least a portion of the device port access into the hollow body, and the membrane is configured to be penetrated by the at least a portion of the device port and to maintain the seal between the membrane and the at least a portion of the device port when the device port is inserted within the hollow body; and
 a lip seal formed by at least a portion of the membrane, the lip seal configured to engage and maintain the seal between the membrane and the at least a portion of the device port when the device port is inserted within the hollow body.

2. The device cleaner of claim 1, further comprising a lid configured to fit over the membrane and the opening of the hollow body.

3. The device cleaner of claim 2, wherein the lid comprises an induction foil seal.

4. The device cleaner of claim 2, wherein the lid further comprises a foil lid liner.

5. The device cleaner of claim 2, wherein the lid is reusable.

6. The device cleaner of claim 2, wherein the lid further comprises at least one protrusion, the membrane comprises an outer surface facing the lid when the lid is affixed over the membrane and the opening of the of the hollow body, the outer surface of the membrane further comprises a cavity, and wherein the at least one protrusion is configured to extend through the lip seal and into the cavity of the membrane when the lid is affixed over the membrane and the hollow body.

7. The device cleaner of claim 2, wherein the lid further comprises one or more threads configured to screw the lid over the membrane and the opening of the hollow body.

8. The device cleaner of claim 2, wherein the lid is bonded or sealed over the membrane and the opening in the hollow body.

9. The device cleaner of claim 2, wherein the lid comprises a top surface, and the top surface of the lid further comprises an identification label.

10. The device cleaner of claim 1, wherein the membrane further comprises a slit configured to be penetrable by the at least a portion of the device port.

11. The device cleaner of claim 1, wherein the membrane comprises an elastic material.

12. The device cleaner of claim 1, wherein when the membrane is penetrated by the at least a portion of the device port, the lip seal is configured to form a seal between the membrane and the inserted portion of the device port to maintain the seal of the hollow body.

13. The device cleaner of claim 1, wherein the device port comprises male connectors, female connectors, medical device luers, medical device hubs, syringes, or any medical device connector comprising at least a portion thereof fitting within the diameter of the opening of the hollow body.

14. The device cleaner of claim 1, wherein when the membrane is penetrated by the device port, the membrane is configured to provide a tight-fit around the device port to physically support and maintain the inserted position of the device port.

15. The device cleaner of claim 1, wherein the membrane further comprises one or more concentric perforations, wherein the hollow body further comprises one or more extrusions extending out of the opening of the hollow body, and wherein the one or more extrusions are configured to mate with at least one of the one or more perforations to affix the membrane over the opening of the hollow body.

16. The device cleaner of claim 15, wherein when the one or more extrusions mate with at least one of the one or more perforations, the one or more extrusions form a rivet with the membrane.

17. The device cleaner of claim 1, wherein the hollow body further comprises an outer surface with one or more grooves to provide the hollow body with a gripping surface.

18. The device cleaner of claim 1, further comprising a removable lid configured to fit over the opening of the hollow body to seal at least the membrane and the disinfecting agent inside the hollow body and away from the external environment.

19. The device cleaner of claim 1, further comprising an absorbent material holding the disinfecting agent.

20. The device cleaner of claim 19, wherein the absorbent material is configured to release the disinfecting agent when the absorbent material is contacted by the inserted portion of the device port inside the hollow body.

21. The device cleaner of claim 19, wherein the absorbent material comprises a sponge, absorbent cotton, polyurethane, polyvinyl alcohol, silicone, cellulose wood fibers, foam, or foamed plastic polymers.

22. The device cleaner of claim 19, wherein the absorbent material is configured to release the disinfecting agent when the absorbent material is engaged by a mechanical force applied by a user against the exterior of the hollow body.

23. The device cleaner of claim 19, wherein the absorbent material is configured to scrub the at least a portion of the device port when the device port is being inserted into the hollow body.

24. The device cleaner of claim 1, wherein the hollow body further comprises an interior surface comprising one or more internal threads, wherein the one or more internal threads is configured to enable the device port to be screwed into the hollow body.

25. The device cleaner of claim 1, wherein the disinfecting agent comprises a form selected from a group consisting of a liquid, a gel, and a hydrogel.

26. The device cleaner of claim 1, wherein the disinfecting agent comprises one or more chemicals selected from a microbial agent, antiseptic fluid, ethyl alcohol, medical grade alcohol, isopropyl alcohol, and povidone iodine.

27. The device cleaner of claim 1, wherein the membrane further comprises a thin portion relative to the surrounding membrane, the thin portion configured to be penetrated by the at least a portion of the device port, and wherein the lip seal is formed by the relatively thicker surrounding membrane and the lip seal is disposed a distance from the thin portion of the membrane.

28. A device cleaner for cleaning an end of a device port, comprising:
   a hollow body with an opening;
   a disinfecting agent within the hollow body;
   a membrane covering the opening of the hollow body, wherein the membrane creates a seal within the hollow body prior to the membrane being penetrated by at least a portion of a device port inserted within the hollow body;
   a lid configured to fit over the membrane and the opening of the hollow body;
   wherein the membrane is configured to be penetrable by the device port to provide the at least a portion of the device port access into the hollow body, the membrane is configured to be penetrated by the at least a portion of the device port and to maintain the seal between the membrane and the at least a portion of the device port when the device port is inserted within the hollow body, and the membrane comprises an outer surface facing the lid when the lid is affixed over the membrane and the opening of the of the hollow body, the outer surface of the membrane further comprises a cavity, the membrane prior to penetration by at least portions of the device port, further comprises a cavity, and
   wherein the lid further comprises at least one protrusion, and wherein the at least one protrusion is configured to extend into the cavity of the membrane when the lid is affixed over the membrane and the hollow body.

29. The device cleaner of claim 28, wherein the lid comprises an induction foil seal.

30. The device cleaner of claim 28, wherein the lid further comprises a foil lid liner.

31. The device cleaner of claim 28, wherein the lid is reusable.

32. The device cleaner of claim 28, wherein the lid further comprises one or more threads configured to screw the lid over the membrane and the opening of the hollow body.

33. The device cleaner of claim 28, wherein the lid is bonded or sealed over the membrane and the opening in the hollow body.

34. The device cleaner of claim 28, wherein the lid comprises a top surface, and the top surface of the lid further comprises an identification label.

35. The device cleaner of claim 28, further comprising a lip seal formed by at least a portion of the membrane, the lip seal configured to engage and maintain the seal between the membrane and the at least a portion of the device port when the device port is inserted within the hollow body.

36. The device cleaner of claim 35, wherein the membrane further comprises a thin portion relative to the surrounding membrane, the thin portion configured to be penetrated by the at least a portion of the device port, and wherein the lip seal is formed by the relatively thicker surrounding membrane and the lip seal is disposed a distance from the thin portion of the membrane.

37. A device cleaner for cleaning an end of a device port, comprising:
   a hollow body with an opening;
   a disinfecting agent within the hollow body;
   an absorbent material holding the disinfecting agent;
   a membrane covering the opening of the hollow body, wherein the membrane creates a seal of the hollow body prior to the membrane being penetrated by at least a portion of a device port inserted within the hollow body;
   wherein the membrane is configured to be penetrable by the device port to provide the at least a portion of the device port access into the hollow body, and the membrane is configured to be penetrated by the at least a portion of the device port and to maintain the seal between the membrane and the at least a portion of the device port when the device port is inserted within the hollow body; and
   a lip seal secured to the hollow body and disposed a distance from the membrane configured to the penetrated by the at least a portion of the device port and on the opposite side of the membrane from the absorbent material holding the disinfecting agent; and
   wherein the lip seal and membrane form a membrane cavity for receiving the at least a portion of the device port.

38. The device cleaner of claim 37, wherein the absorbent material is configured to release the disinfecting agent when the absorbent material is contacted by the at least a portion of the device port inserted into the hollow body.

39. The device cleaner of claim 37, wherein the absorbent material comprises a sponge, absorbent cotton, polyurethane, polyvinyl alcohol, silicone, cellulose wood fibers, foam, or foamed plastic polymers.

40. The device cleaner of claim 37, wherein the absorbent material is configured to release the disinfecting agent when the absorbent material is engaged by a mechanical force applied by a user-against the exterior of the hollow body.

41. The device cleaner of claim 37, wherein the absorbent material is configured to scrub the at least a portion of the device port when the device port is being inserted into the hollow body.

42. The device cleaner of claim 37, further comprising a lid covering the lip seal, the lid further comprising at least one protrusion extending through the lip seal and into the membrane cavity.

43. The device cleaner of claim 42, wherein the hollow body comprises a sidewall extending beyond the membrane to form a rim of the hollow body opening and wherein membrane and lip seal are secured over the rim of the hollow body opening.

44. The device cleaner of claim 42, wherein the hollow body comprises a sidewall extending beyond the membrane to form a rim of the hollow body opening and wherein the lid is secured over the rim of the hollow body opening.

45. The device cleaner of claim 42, wherein the lid protrusion and lip seal are circular and matingly engage together.

\* \* \* \* \*